(12) United States Patent
Huang et al.

(10) Patent No.: US 6,489,466 B2
(45) Date of Patent: Dec. 3, 2002

(54) C-3' PROTECTED MONOMERIC NUCLEOTIDES AND SYNTHESIS OF OLIGONUCLEOTIDES ON SOLID SUPPORT

(75) Inventors: Yih Huang, Lexington, MA (US); Tai-Nang Huang, Lexington, MA (US); Ming Shen, Guilford, CT (US)

(73) Assignee: Linden Technologies, Inc., Woburn, MA (US)

( * ) Notice: Subject to any disclaimer, the term of this patent is extended or adjusted under 35 U.S.C. 154(b) by 0 days.

(21) Appl. No.: 09/770,886

(22) Filed: Jan. 26, 2001

(65) Prior Publication Data

US 2001/0044530 A1 Nov. 22, 2001

Related U.S. Application Data

(60) Provisional application No. 60/178,720, filed on Jan. 28, 2000, and provisional application No. 60/189,804, filed on Mar. 16, 2000.

(51) Int. Cl.[7] .......................... C12Q 1/68; C07H 19/00; C07H 21/00; C07H 21/02; C07H 21/04
(52) U.S. Cl. .................. 536/25.3; 435/6; 536/22.1; 536/23.1; 536/25.31; 536/25.33; 536/25.34
(58) Field of Search .............................. 435/6; 536/22.1, 536/23.1, 25.3, 25.31, 25.33, 25.34

(56) References Cited

U.S. PATENT DOCUMENTS

| | | | |
|---|---|---|---|
| 4,500,707 A | 2/1985 | Caruthers et al. | 536/27 |
| 4,828,979 A | 5/1989 | Klevan et al. | 435/6 |
| 5,218,103 A | 6/1993 | Caruthers et al. | 536/25.33 |

(List continued on next page.)

FOREIGN PATENT DOCUMENTS

| | | |
|---|---|---|
| EP | 0 216 357 A2 | 4/1987 |
| WO | WO 92/03461 | 3/1992 |
| WO | WO 98/41531 | 9/1998 |

OTHER PUBLICATIONS

Balgobin and Chattopadhyaya, "Solid Phase Synthesis of DNA under a Non–Depurinating Condition with a Base Labile 5'–Protecting Group (Fmoc) using Phosphiteamidite Approach", *Nucleosides & Nucleotides* 6(1&2):461–463 (1987).

Bannwarth and Iaiza, "Laboratory Methods: A System for the Simultaneous Chemical Synthesis of Different DNA Fragments on Solid Support", *DNA* 5(5):413–419 (1986).

(List continued on next page.)

*Primary Examiner*—Jezia Riley
(74) *Attorney, Agent, or Firm*—Fish & Richardson P.C.

(57) ABSTRACT

Immobilized nucleotide primers of this invention include a modified nucleotide tethered to a support substrate through a linking group. In particular, the modified nucleotide is constructed such that the C-5' end of the nucleotide is tetherable to the linking group and the protected C-3' end is available for further controlled modification, e.g., addition of other nucleotides in specific sequences to the immobilized nucleotide primer. Additionally, the linking group is of sufficient length to allow the immobilized nucleotide primer to be used to synthesize and screen arrays of oligonucleotides, e.g., enzymatic C-3' primer extension.

39 Claims, 7 Drawing Sheets

U.S. PATENT DOCUMENTS

| | | | |
|---|---|---|---|
| 5,252,296 A | 10/1993 | Zuckermann et al. | 422/116 |
| 5,270,170 A | 12/1993 | Schatz et al. | 435/7.37 |
| 5,424,186 A | 6/1995 | Fodor et al. | 435/6 |
| 5,432,018 A | 7/1995 | Dower et al. | 435/5 |
| 5,489,678 A | 2/1996 | Fodor et al. | 536/22.1 |
| 5,510,270 A | 4/1996 | Fodor et al. | 436/518 |
| 5,529,456 A | 6/1996 | Brennan | 422/131 |
| 5,723,599 A | 3/1998 | Klem et al. | 536/25.3 |
| 5,744,101 A | 4/1998 | Fodor et al. | 422/131 |
| 5,744,305 A | 4/1998 | Fodor et al. | 435/6 |
| 5,889,165 A | 3/1999 | Fodor et al. | 536/22.1 |
| 5,908,926 A * | 6/1999 | Pirrung et al. | 546/25.34 |
| 5,985,551 A | 11/1999 | Brennan | 435/6 |
| 6,001,311 A | 12/1999 | Brennan | 422/131 |
| 6,022,714 A | 2/2000 | Brown et al. | 435/91.1 |
| 6,028,189 A | 2/2000 | Blanchard | 536/25.3 |
| 6,177,558 B1 | 1/2001 | Brennan et al. | 536/25.3 |
| 6,210,894 B1 | 4/2001 | Brennan | 435/6 |
| 6,337,393 B1 | 1/2002 | Brennan et al. | 536/25.3 |

OTHER PUBLICATIONS

McBride and Caruthers, "An Investigation of Several Deoxynucleoside Phosphoramidites Useful for Synthesizing Deoxyoligonucleotides", *Tetrahedron Letters* 24(3):245–248 (1983).

Sonveaux, "The Organic Chemistry Underlying DNA Synthesis", *Bioorganic Chemistry* 14:274–325 (1986).

Zon et al., "Analytical studies of 'mixed sequence' oligodeoxyribonucleotides synthesized by competitive coupling of either methyl–or β–cyanoethyl–N,N–diisopropylamino phosphoramidite reagents, including 2'-deoxyinosine", *Nucleic Acids Research* 13(22):8181–8196 (1985).

Amarnath, V. et al., "Chemical Synthesis of Oligonucleotides", *Chemical Reviews*, vol. 77,pp. 183–217, 1997.

Amit, B. et al., "Photosensitive Protecting Groups of Amino Sugars and Their Use in Glycoside Synthesis. 2–Nitrobenzyloxycarbonylamino and 6–Nitroveratryloxycarbonylamino Derivatives", *J. Org. Chem.*, vol. 39, pp. 192–196, 1974.

Bains, W. et al., "A Novel Method for Nucleic Acid Sequence Determination", *J. Theor. Biol,.* vol. 135, pp. 303–307, 1988.

Beaucage, SL. et al., "Advances in the Synthesis of Oligonucleotides by the Phosphoramidite Approach", *Tetrahedron*, vol. 48, pp. 2223–2311, 1992.

Bunin, BA. Et al., "The Combinatorial Synthesis and Chemical and Biological Evaluation of a 1,4–Benzodiazepine Library", *Proc. Natl. Acad. Sci. USA*, vol. 91, pp. 4708–4712, 1994.

Drmanac, R. et al. "Sequencing of Megabase Plus DNA by Hybridization: Theory of the Method", *Genomics*, vol. 4, pp. 114–128, 1989.

Fodor, SPA. et al. "Light–Directed, Spatially Addressable Parallel chemical Synthesis", *Science*, vol. 251, pp. 767–773, 1991.

Gait, MJ. *Oligonucleotide Synthesis: A Practical Approach*, IRL Press Oxford, 1984.

McGall, G. et al., "Light–Directed Synthesis of High–Density Oligonucleotide Arrays Using Semiconductor Photoresists", *Proc. Natl. Acad. Sci. USA*, vol. 93, pp. 13555–13560, 1996.

Ohtsuka, E. et al., "Recent Developments in the Chemical Synthesis of Polynucleotides", *Nucleic Acids Research*, vol. 10, pp. 6553–6570, 1982.

Patchornik, A. et al., "Photosensitive Protecting Groups", *Journal of the American Chemical Society*, vol. 92, pp. 6333–6335, 1970.

Ramsay, G., "DNA Chips: State–of–the Art" *Nature Biotechnology*, vol. 16, pp. 40–44, 1998.

Schena, M. et al., "Quantitative Monitoring of Gene Expression Patterns with a Complementary DNA Microarray", *Science*, vol. 270, pp. 467–470, 1995.

Singh–Gasson, S., "Maskless Fabrication of Light–Directed Oligonucleotide Microarrays Using a Digital Micromirror Array" *Nature Biotechnology*, vol. 17, pp. 974–978, 1999.

Koga et al., "Synthesis and Physiochemical Properties of Alternating α,β–Oligodeoxyribonucleotides with Alternating (3'–3')–and(5'–5')–Internucleotidic Phosphodiester Linkages", J. Org. Chem. 60:1520–1530, 1995.

Kwiatkowski et al., "Inversion of In Situ Synthesized Oligonucleotides: Improved Reagents for Hybridization and Primer Extension in DNA Microarrays", Nucleic Acids Research 27:4710–4714, 1999.

Pirrung et al., "Inverse Phosphotriester DNA Synthesis Using Photochemically–Removable Dimethyoxybenzoin Phosphate Protecting Groups", J. Org. Chem. 61:2129–2136, 1996.

Shchepinov et al., "Steric Factors Influencing Hybridisation of Nucleic Acids to Oligonucleotide Arrays", Nucleic Acids Research 25:1155–1161, 1997.

* cited by examiner where Z can be halogen or mixed anhydride;
Base can be A, T, G, C or I for Inosine.

DIPEA: Diisopropylethylamine
DBU: 1,8-Diazabicyclo[5,4,0]undec-7-ene

Figure 7

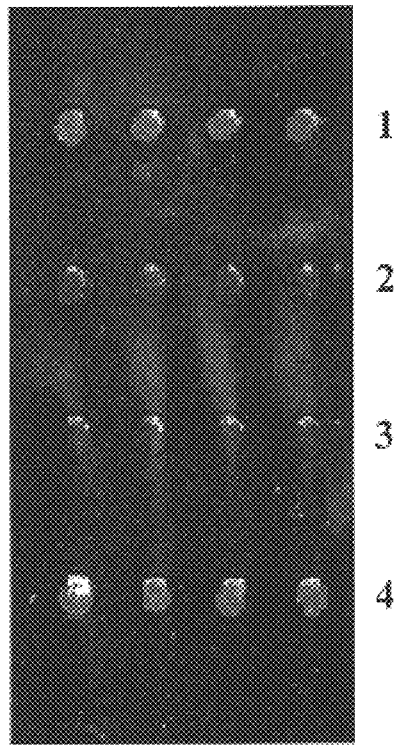

Row 1: Treatment of Cy3-OH with surface phosphoramidite containing polyethylene glycol linker (PEG-O-PAM + Cy3-OH) on a the glass substrate.

Row 2: Treatment of Cy3-OH with substrate surface containing photo-protecting group. No surface phosphoramidite exists (PEG--5'-O-T-3'-O-MBNPEOC + Cy3-OH).

Row 3: Treatment of Cy3-OH with surface C-3' hydroxyl group obtained after photo-deprotection on C-3' oxygen of covalently bound nucleotides on substrate surface (PEG--5'-O-T-3'-OH + Cy3-OH).

Row 4: Treatment of Cy3-OH with surface phosphoramidite on C-3' oxygen of covalently bound nucleotides on substrate surface (PEG--5'-O-T-3'-O-PAM + Cy3-OH).

C-3' PROTECTED MONOMERIC NUCLEOTIDES AND SYNTHESIS OF OLIGONUCLEOTIDES ON SOLID SUPPORT

CROSS-REFERENCE TO RELATED APPLICATION

Pursuant to 35 U.S.C. §120, this application is a continuation of, and claims priority from U.S. application Ser. Nos. 60/178,720 and 60/189,804, filed Jan. 28, 2000 and Mar. 16, 2000, respectively.

BACKGROUND

Of all the genes in a genome, only a small fraction are expressed in any individual cell. The temporal and spatial regulation in gene expression determines life processes. Many pathological developments, such as oncogenesis, are driven by gene expression. Identification of multiple genetic alterations as they occur in the genome is critical to understanding the molecular genetic events. Sequence analysis of nucleic acid molecules is essential to understanding and diagnosing disorders. Genetic alterations identified as being related to diseases can then be used as a guide for drug discovery. In the past two decades, the invention of techniques for immobilizing nucleic acid molecules on a solid phase has had a profound impact on the progress of the nucleic acid analysis, such as the use of DNA chips for gene expression analysis and solid phase primer extension for single nucleotide polymorphism analysis. Automation of solid phase oligonucleotide synthesis has helped propel the advancement of molecular biology, which undoubtedly has laid the foundation of the modern understanding of life sciences.

SUMMARY

In general, the present invention features a method for producing an immobilized oligonucleotide attached to a substrate via a C-5' position and having a terminal C-3' position.

In one aspect, this invention is directed to a method of producing an immobilized oligonucleotide on a substrate to which a first nucleotide is covalently attached via its C-5' oxygen. The first nucleotide can be a nucleotide monomer or the 5' terminal nucleotide of a nucleotide polymer. In general, such a first nucleotide includes a modified nucleotide tethered to a support substrate through a linking group. In particular, the modified nucleotide is constructed such that the C-5' end of the nucleotide is tetherable to the linking group and the C-3' end is available for further controlled modification, e.g., addition of other nucleotides in specific sequences to the immobilized nucleotide. In the case of adding a nucleotide monomer as the first nucleotide, the C-3' end is the C-3' of the nucleotide monomer. In the case of adding a nucleotide polymer as the first nucleotide, the C-3' end is the C-3' of the terminal nucleotide of the polymer. Additionally, the linking group is of sufficient length to allow the immobilized nucleotide to be used to synthesize and screen arrays of nucleotide oligomers, e.g., enzymatic C-3' primer extension.

In another aspect, the invention provides a method for in situ solid phase oligonucleotide synthesis with C-5' attached to the substrate, thereby producing oligonucleotides which are a polymer of nucleotides. The method covers an in situ deprotection-activation-coupling cycle of oligonucleotide synthesis that includes covalently coupling a modified nucleotide via its C-5' oxygen to an immobilized hydroxyl, wherein the modified nucleotide includes a C-3' photolabile protecting group and a C-5' hydroxyl group, and also wherein the immobilized hydroxyl group is activated with a phosphorous activating group. The synthesis includes sequentially deprotecting photolabile group from the C-3' oxygen of an immobilized nucleotide at terminus, activating the C-3' oxygen at terminus, in situ, with an activating phosphorous group, and coupling C-3' protected nucleotides to the activated nucleotide at terminus. Optionally, the cycles of deprotecting, activating, and coupling can be repeated until a desired oligonucleotide is obtained. Typically, the immobilized C-3' oxygen is activated with a phosphorous group such as a phosphoramidite, $[(i-Pr)_2N]POCH_2CH_2CN$. The produced oligonucleotide can be further involved in enzyme-catalyzed reactions, e.g., polymerase mediated primer extension.

In further another aspect, the invention provides a method for an oligonucleotide synthesis in a direction of 5' to 3', thereby producing oligonucleotides that are a set of specific nucleotides. The method covers a deprotection-activation-coupling oligonucleotide synthesis which consists of a nucleotide or an oligonucleotide having a free terminal C-3' hydroxyl and a terminal C-5' that is blocked by a group, wherein the free terminal C-3' hydroxyl is activated with a phosphorous activating group. The synthesis includes sequentially deprotecting a photolabile protecting group from the C-3' oxygen of a nucleotide at terminus, activating the C-3' oxygen, in situ, with an activating phosphorous group, and coupling another C-3' photolabile protected nucleotides to the activated nucleotide at terminus. Optionally, the cycles of deprotecting, activating, and coupling can be repeated until a desired oligonucleotide is obtained. Typically, the C-3' oxygen is activated with a phosphorous group such as a phosphoramidite, e.g., $[(i-Pr)_2N]POCH_2CH_2CN$.

The invention also features an array. The array includes a substrate having a plurality of addressable sites. Each of the sites of the plurality has an oligonucleotide covalently attached to the substrate via its C-5' oxygen atom. Each site of the plurality can be directly adjacent to at least one other site. The sequence of each oligonucleotide of a site can be unique among the plurality. Addressable sites other than the sites of the plurality can be disposed on the array. The array can have a density of addresses and oligonucleotides described below. A spatially selective irradiation technique can be used to make such an oligonucleotide array. Generally, the method covers an in situ deprotection-activation-coupling oligonucleotide synthesis to covalently couple the C-5' position of a non-immobilized nucleotide or oligonucleotide to a substrate to form an immobilized oligonucleotide having a photolabile group protected C-3' oxygen available for the attachment of subsequent C-3' protected nucleotides. The substrate includes a plurality of immobilized nucleotide starters arranged on the substrate as a 2-dimensional array. The synthesis for covalently coupling the C-5' position of a non-immobilized nucleotide or oligonucleotide to a substrate includes selectively removing photolabile groups from a subset of immobilized nucleotides or oligonucleotides in the array by irradiating the subset to produce an hydroxyl group at the C-3' terminus. The C-3' hydroxyl group on the immobilized nucleotide at terminus can be activated again in-situ to form phosphoramidite for coupling the next non-immobilized nucleotide or oligonucleotide having a C-5' hydroxyl group. Alternatively, the C-3' hydroxyl group on the immobilized nucleotide can couple with a non-immobilized nucleotide or oligonucleotide having an C-5' activated group and a C-3' photolabile protecting group. The sequence and the length of the immobilized oligonucleotide can be chosen for specific applications. Photolabile protecting groups include, but are not limited to, NVOC, MBNPEOC, and MeNPOC.

Within the scope of this invention is a method to synthesize a nucleotide that is activated at C-5' and photolabile group-protected at C-3'. The method includes protecting the C-5' hydroxyl group, attaching a photolabile protecting group to the C-3' oxygen, deprotecting the C-5' hydroxyl group, and attaching an activated phosphorous group to the C-5' oxygen of a ribonucleic or deoxyribonucleic acid. Typically, the activated phosphorous group is phosphoramidite, i.e., $[(i-Pr)_2N]POCH_2CH_2CN$. In general, the stereochemistry at C-1, i.e., where the base is attached to the sugar ring, can be selected to improve the synthetic yield of the C-5' activated, C-3' photolabile group protected nucleotide. Also contained within the scope of this invention is a method to covalently couple the C-5' activated terminus of a monomeric nucleotide to a surface modified functional group on a substrate to form an immobilized nucleotide primer with an C-3' oxygen available for the attachment of the next C-5' activated, C-3' protected nucleotide.

The invention features a C-3' protected nucleotide having the formula

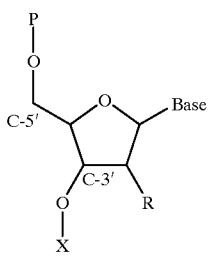

wherein X is selected from the group consisting of a photolabile protecting group and a chemically labile protecting group; R is selected from the group consisting of hydrogen and hydroxyl; P is selected from the group consisting of hydrogen, a phosphorous activating group, and a phosphate or derivative thereof, and Base is selected from the group consisting of pyrimidine, purine, and derivatives thereof.

C-3' protected nucleotide can have the formula

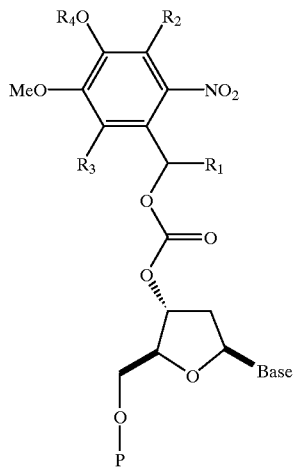

wherein $R_1$, $R_2$, $R_3$ each independently is selected from the group consisting of hydrogen, C1–C10 alkyl, C2–C10 alkenyl, aryl, benzyl, and C1–C10 alkoxyl; $R_4$ is selected from the group consisting of C1–C10 alkyl, C2–C10 alkenyl, aryl, and benzyl; and P is selected from the group consisting of hydrogen and $[(i-Pr)_2N]POCH_2CH_2CN$.

The C-3' protected nucleotide can also have the formula

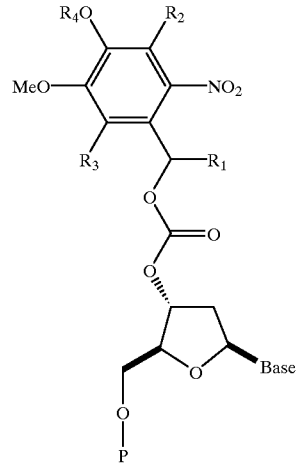

wherein $R_1$, $R_2$, $R_3$ each independently is selected from the group consisting of hydrogen, C1–C10 alkyl, C2–C10 alkenyl, aryl, benzyl, and C1–C10 alkoxyl; $R_4$ is selected from the group consisting of C1–C10 alky, C2–C10 alkenyl, aryl, and benzyl; and P is selected from the group consisting of hydrogen and $[(i-Pr)_2N]POCH_2CH_2CN$.

Embodiments of the aspects of the invention may include one or more of the following. The terminal position of the linking group for coupling with a C-3' protected nucleotide is a functional group. The functional group is activated in-situ to form a phosphoramidite. The terminal phosphoramidite is coupled with a C-5' hydroxyl group of a nucleotide bearing a photolabile group protecting the C-3' oxygen. The immobilized monomeric nucleotide is covalently attached to the linking group via the C-5' oxygen. Preferably, the nucleotide of the immobilized monomeric nucleotide is deoxyinosine.

The invention provides one or more of the following advantages. The in situ deprotection-activation-coupling oligonucleotide synthesis is economical and versatile and generates solid phase phosphoramidite that exhibits unexpected high efficiency in coupling with sequentially added C-3' photolabile group protected nucleotides. The in situ deprotection-activation-coupling oligonucleotide synthesis provides high yield in-situ surface activation, e.g., substantially quantitative and stable, for forming surface phosphoramidite at the immobilized C-3' position. The photolabile group-protected C-3' nucleotides provide sufficient solubility in organic solvents for conducting nucleotide coupling reactions and have a short half-life that can improve the efficiency of photo-deprotection at the C-3' position. Additionally, excess C-3' photolabile group protected nucleotides can be recycled and directly used in the later coupling reactions, whereas coupling methods for coupling non-immobilized, phosphoramidite-containing nucleotides require a large excess of the phosphoramidite containing nucleotide (up to 50 folds) which subsequently decomposes in the coupling reaction. Inosine is known to help stabilize hybridization with another DNA molecule.

More than a single disease associated target gene can be tested to reveal more detailed disease information by producing DNA chips which contain a series of spatially arrayed specific immobilized nucleotide primers. Testing spatially arrayed immobilized nucleotide primers on DNA chips also will provide more precise disease diagnostic data of a patient and therefore more efficient treatment. Use of the PCR technique to identify the target genes with the primer-containing DNA chips is more reliable than hybridization alone. Currently, PCR-based disease diagnostics have not been widely used because of the cost concern. Thus, the immobilized oligonucleotides containing DNA chips of this invention would be more useful, accurate and relatively inexpensive.

Due to the orientation of the immobilized oligonucleotides, bound C-5' and terminal C-3', the immobilized oligomer acts as an oligonucleotide array for use in primer extensions in the presence of an enzyme, such as polymerase, DNA templates, and nucleotide triphosphates. The ability to perform primer extension in an array format has many important applications including single nucleotide polymorphism (SNP) analysis in pharmacogenomics, transcriptional profiling and on-chip gene sequencing. Unlike immobilized oligonucleotides having C-3' bound and C-5' at the terminal position which can only be used in hybridization for genetic analysis, the immobilized oligonucleotides having C-5' bound and C-3' at the terminal position can be used as primers for polymerase mediated primer extension. The enzymes used in the primer extension can also avoid mismatches during hybridization but before the enzyme mediated primer extension occurs to provide an advantage of proofreading the matched sequences of the DNA probes. The proofreading ability of the enzyme forms the basis of the detection of single nucleotide polymorphism (SNP).

The details of one or more embodiments of the invention are set forth in the accompanying drawings and the description below. Other features, objects, and advantages of the invention will be apparent from the description and drawings.

DESCRIPTION OF DRAWINGS

FIG. 7 shows the relative fluorescence of immobilized nucleotides including C-3' photolabile protecting, hydroxyl, and phosphoramidite groups.

DETAILED DESCRIPTION

Attachment of a first nucleotide to a substrate

Figure 1:
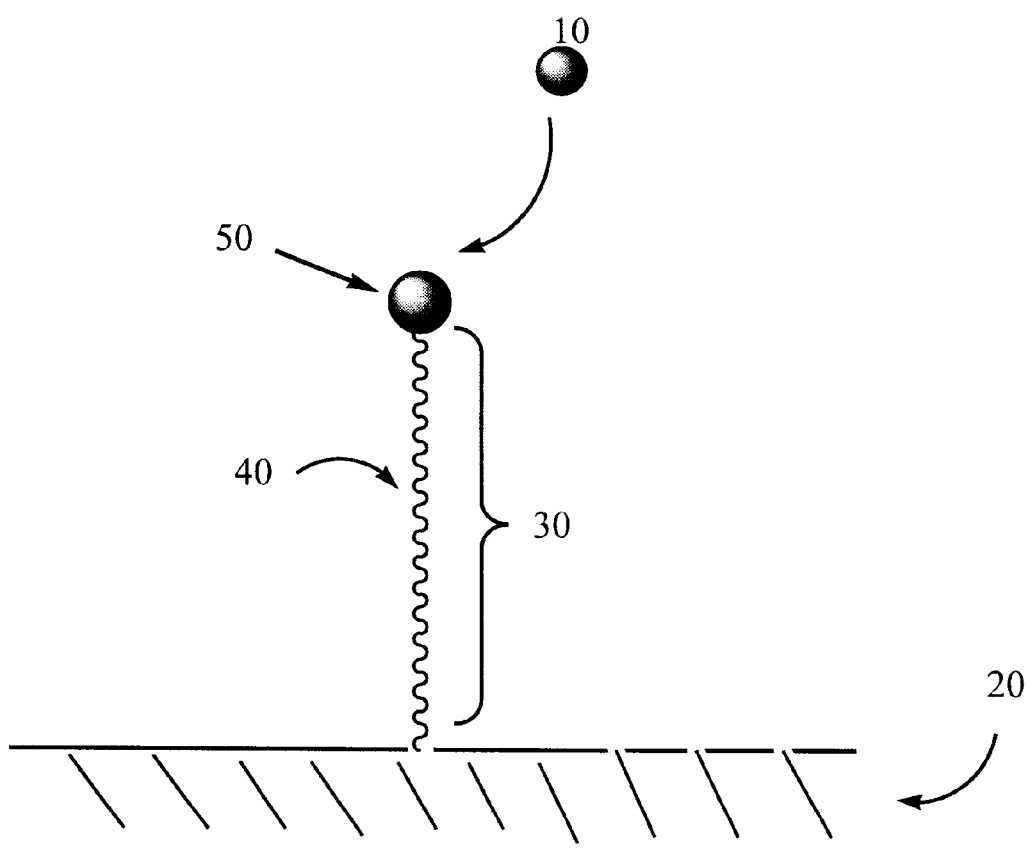
FIG. 1 is a schematic representation of a covalently immobilized nucleotide primer.

Referring to FIG. 1, an immobilized oligonucleotide 10 includes at least one modified nucleotide 50 connected to a substrate 20 via a linking group 40. The distance, L, from substrate 20 to modified nucleotide 50, is determined by the length of linking group 40. The exact length of linking group 40 is selected such that immobilized nucleotide primer 10 can be used in combinatorial chemical assays to synthesize and screen arrays of nucleotide oligomers. Specifically, the optimal length is determined by the efficiency both of phosphoramidit coupling of nucleotides to modified nucleotide 50 and of enzyme-catalyzed reactions, e.g., polymerase mediated primer extension. The first step of an enzyme-catalyzed reaction is hybridization of cDNA templates with immobilized nucleotide starter 10. The efficiency of hybridization can be affected by the steric factors contributed by the substrate 20. In addition, the hydrophilic environment surrounding modified nucleotide 50 is also important for enzymatic reactivity.

The linking group can be formed from any number or combination of atoms or molecules to provide an optimal distance between the substrate and the first modified nucleotide. For example, the linking group can be formed of organic polymers, e.g., repeating units of polyethylene glycol, —$(OCH_2CH_2)n$—O—, to create acceptable hydrophilic conditions and appropriate length, L. In general, polyethylene glycol linker groups have between about 3 to about 30 repeating units. Typically, the linking group includes a functional group which connects to modified nucleotide 50. Examples of functional groups include, but are not limited to, hydroxyl and amino.

The substrate is made from any material having a rigid or semi-rigid surface. In general, the substrate material is resistant to the variety of synthesis and analysis conditions of the combinatorial chemical assays. Examples of substrate materials include, but are not limited to glass, quartz, silicon, gallium aresenide, polyurethanes, polyimides, and polycarbonates. Of course, the substrate material can be a composite of one or more materials. For example, glass supports, i.e., glass slides, can be coated with a polymer material to produce a substrate. Additionally, the support can be made in any shape, e.g., flat, tubular, round, and include ridges or grids to create a patterned substrate. Patterned substrates can be produced, for example, by known photolithographic techniques.

The first modified nucleotide 50 of this invention is attached to the solid substrate via a linker and is formed from a precursor. A typical structure of the precursor is shown in formula (1),

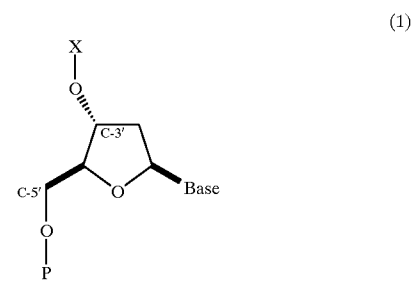

(1)

where X is a photolabile protecting group. P can be either hydrogen or an activated phosphorous group. Bases attached to the sugar ring include, but are not limited to, pyrimidine, purine, and derivatives thereof such as adenine (A), guanine (G), thymine (T), cytosine (C), and inosine (I). Although shown with specific stereochemistry, the modified nucleotide can have different stereochemistry at each of the carbons in the deoxyribose. For example, base can be attached to the ring either in the α or β position. In some embodiments, the modified nucleotide includes a hydroxyl group in the C-2' position to form a ribose ring.

The activated phosphorous group is a reactive derivative having a high coupling efficiency, examples of which include, but are not limited to, phosphate-triesters, phosphoramidite, or the like. See, for example, "Oligonucleotide Synthesis: a Practical Approach" by Gait. The photolabile protecting groups protect the nucleotide from reacting with other nucleotides or other chemical species and are photoactivatable, i.e., removable by exposure to an energy source such as UV radiation, visible radiation, electric potentials, and electron beams. The properties and uses of photolabile groups can be found, for example, in *J. Amer. Chem. Soc.* (1970) 92:6333 by McCray et al.; in *J. Org. Chem.* (1974) 39:192 by Amit et al.; and in U.S. Pat. No. 5,889,165.

In some embodiments, the first modified nucleotide 50 can include chemically labile protecting groups at the C-3' oxygen to protect the nucleotide from reacting with other nucleotides or other chemical species. Examples of chemically labile protective groups include, but are not limited to, 4,4'-dimethoxytrityl (DMT), fluorenylmethoxycarbonyl (FMOC), t-butyl esters, and t-butyl ethers. Chemically labile protecting groups are removable by any suitable chemical method, such as acid hydrolysis. Chemically labile protecting groups and chemical methods to remove these groups are described in, for example, Greene's "Protective Groups in Organic Chemistry," 2$^{nd}$ Ed., published by John Wiley & Sons, New York, N.Y., 1991. Of course, the chemically labile group and the chemical conditions necessary to remove it are selected such that other linkages in the oligonucleotide, such as the connection of the first nucleotide to the linking group, are not affected when the chemically labile group is removed under specific chemical conditions.

Novel nucleotides with a C-3' photolabile protecting group

Examples of C-3' photolabile groups protected nucleotides of this invention include compounds of the following formula (2)

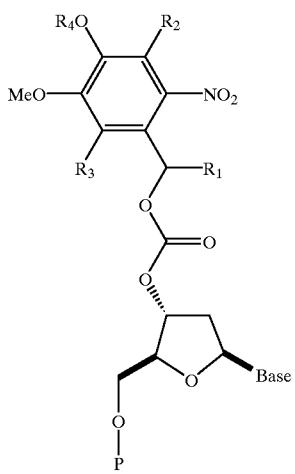

(2)

where $R_1$, $R_2$, $R_3$ each can independently be a hydrogen atom, a lower alkyl, alkenyl, aryl, benzyl or alkoxyl. $R_4$ can be a lower alkyl, alkenyl, aryl or benzyl. P can be a hydrogen atom or phosphoramidite.

Examples of C-5' phosphorous activated, C-3' photolabile group protected nucleotides of this invention include compounds of formulae (3) and (4)

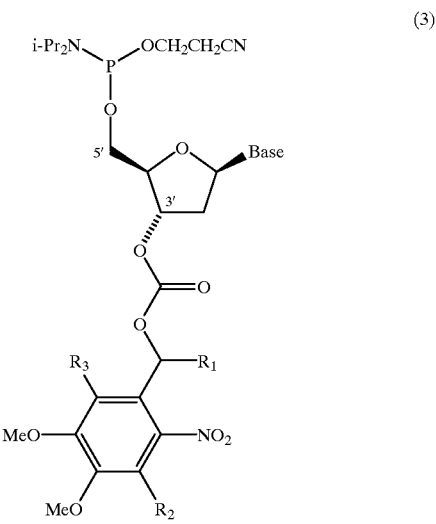

(3)

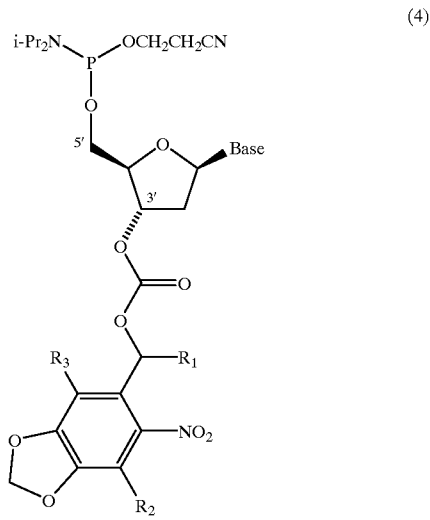

(4)

where R1, R2 and R3 each independently can be a hydrogen atom, a C1–C10 alkyl, C2–C10 alkenyl, aryl, benzyl, C1–C10 alkoxyl or nitro group.

The C-3' photolabile group protected nucleotides of this invention are produced by first temporarily protecting the C-5' hydroxyl group, attaching a photolabile protecting group to the C-3' oxygen, and then removing the C-5' temporary protecting group to form a free hydroxyl group. See formula (2). If a C-5' phosphorous activated group is desired, the C-5' hydroxyl group is activated with an phosphorous activating precursor such as chloro-N,N-diisopropylamine-β-cyanoethoxyphosphine or bis-N,N-diisopropylamine-β-cyanoethoxyphosphine to form the C-5' phosphoramidite compounds in formulae (3) and (4). In general, the stereochemistry at C-1 can be selected, i.e., the base is either at the α or β position, to improve the synthetic yield of the C-3' photolabile group protected nucleotides.

Figure 2:
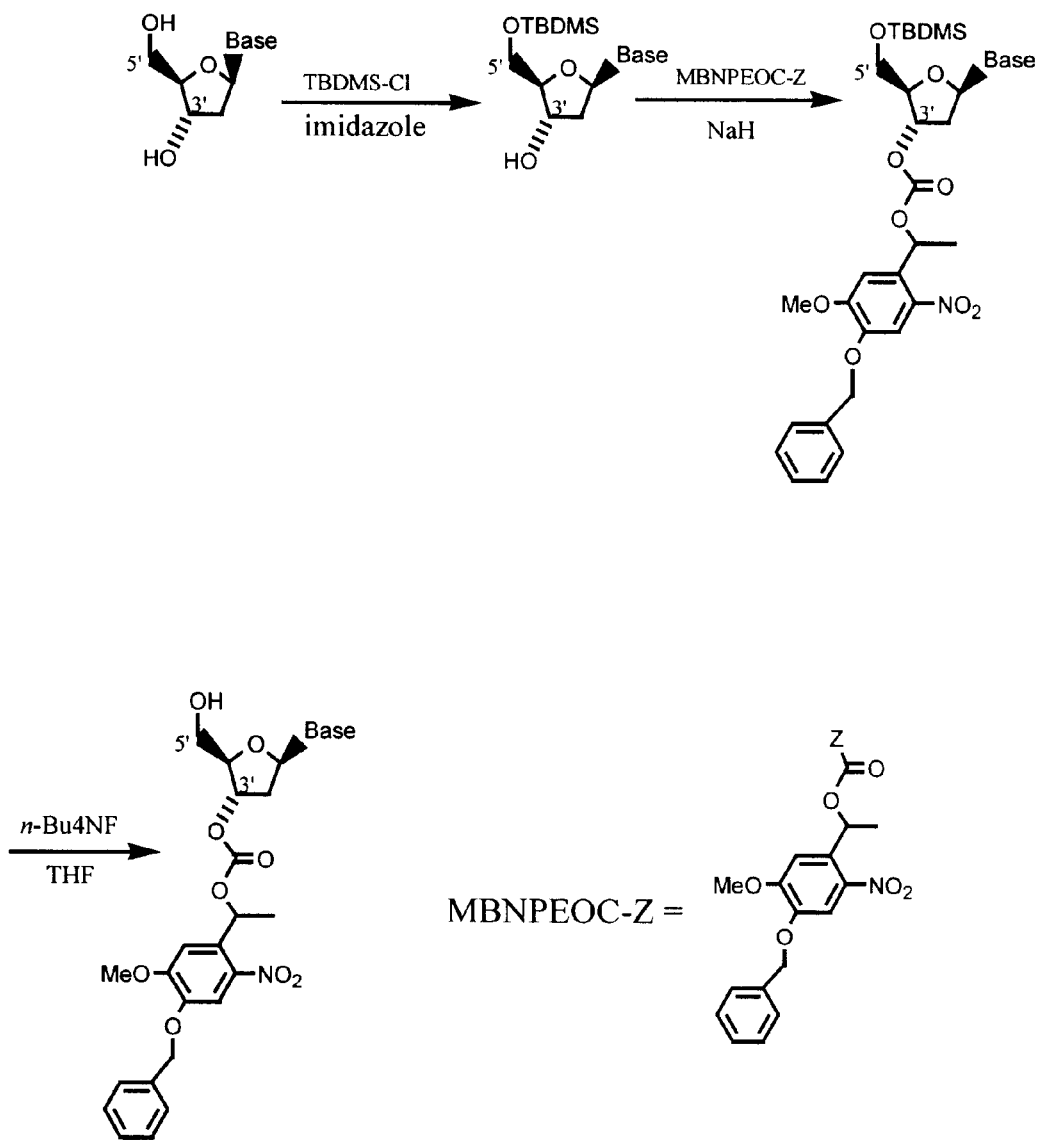
FIG. 2 is a synthetic scheme for producing a monomeric nucleotide having a C-3' photolabile protecting group.

Referring to the synthetic scheme shown in FIG. 2, the C-5' oxygen of deoxyribonucleic acid is protected with a t-butyldimethylsilyl group (TBDMS). Due to steric hindrance, the TBDMS group reacts with the C-5' oxygen rather than the C-3' oxygen. Additionally, the reactivity of the C-3' hydroxyl group, i.e., a secondary alcohol, typically, is less than the reactivity of the C-5' hydroxyl group, i.e., a primary alcohol. Once the C-5' is protected with TBDMS, the C-3' oxygen can be protected with a photolabile protecting group, such as (R,S)-1-(3-methoxy-4-benzyloxy-6-nitrophenyl)ethyl chloroformate to form 5'-O-t-butyldimethylsilyl-3'-O-[(R,S)-(1-(3-methoxy-4-benzyloxy-6-nitrophenyl)-ethoxy)carbonyl]-$N^6$-benzoyl-2'-deoxynucleotides. In general, a photolabile protecting group normally reacts at the C-5' hydroxyl group. However, protecting the C-5' oxygen with TBDMS without protecting the C-3' oxygen permits the photolabile protecting group to attach to the oxygen at C-3' rather than C-5'. The temporary protecting group TBDMS can then be removed via tetrabutyl ammonium fluoride to afford a free hydroxyl group at the C-5' position as shown in formula (1) where P is hydrogen. If a C-5' phosphorous activated group is desired, the free C-5' hydroxl group can be reacted with chloro-N,N-diisopropylamine-β-cyanoethoxyphosphine to produce a C-5' phosphoramidit group. The synthesis shown in FIG. 2, of course, is applicable to ribonucleotides, as well as other phosphorous activating groups and photolabile and chemically protecting groups described herein.

Synthesis of an oligonucleotide

Figure 3:
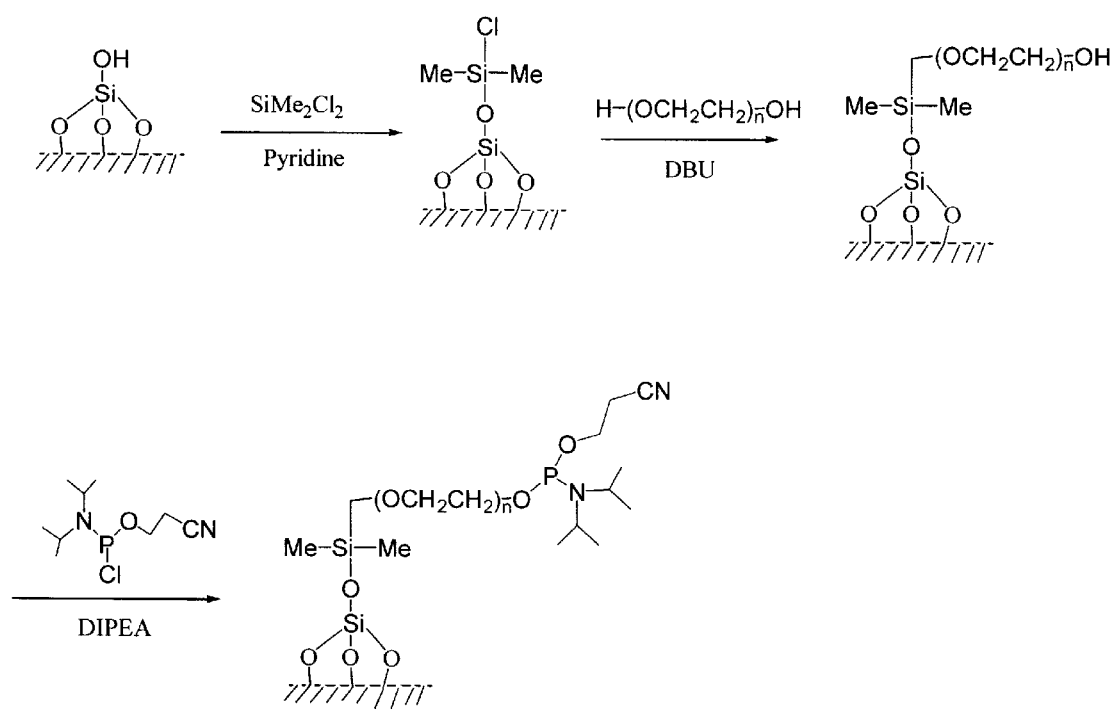
FIG. 3 is a schematic representation of in-situ activation of the surface hydroxyl group.
Figure 4:
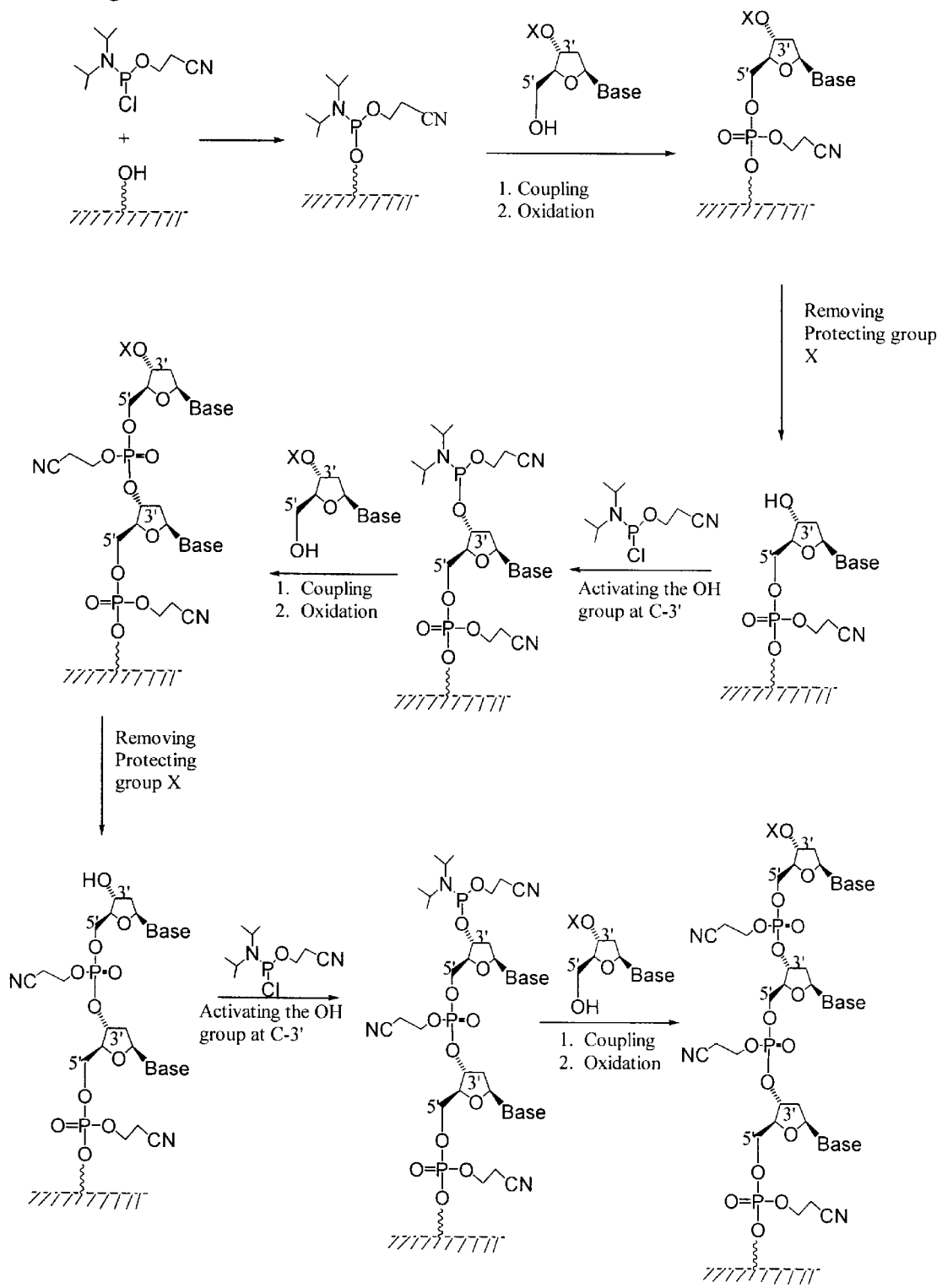
FIG. 4 is a schematic representation of an in-situ deprotecting-activating-coupling synthesis.

Referring to FIGS. 3 and 4, an in situ deprotection-activation-coupling oligonucleotide synthesis includes reacting a terminal hydroxide of the linker group with an activating phosphorous group, such as chloro-N,N-diisopropylamine-β-cyanoethoxyphosphine in the presence of a tertiary amine, to immobilize the activating phosphorous group onto the substrate. After activating the surface hydroxyl group to form a surface phosphoramidite, a modified nucleotide having a free C-5' hydroxyl group can be coupled with the phosphoramidite on the solid surface. The C-5' hydroxide of a modified nucleotide attacks the immobilized activating phosphorous group, in this case a phosphoramidite group, thereby covalently attaching the nucleotide via C-5' to the substrate through the linker group.

In situ deprotecting-activating-coupling oligonucleotide synthesis includes sequentially deprotecting the C-3' oxygen of the immobilized primer nucleotide or oligomer, activating the C-3' oxygen, in situ, with an activating phosphorous group, and coupling a C-3' protected modified nucleotide of formula 1 in which P is hydrogen to the immobilized nucleotide or oligomer. The cycles of deprotecting, activating, coupling are repeated until a desired sequence is obtained. In particular, the nucleophilic attack of the C-5' free primary alcohol of the next monomeric nucleotide at the activating phosphorous group, i.e., the phosphoramidite activated C-3' position, of the immobilized nucleotide shows an improved coupling efficiency relative to the secondary alcohol attack shown such as when a C-3' secondary alcohol attacks an activating phosphorous group on the C-5' oxygen of a modified monomer.

As shown in FIG. 4, after covalently connecting the first nucleotide to the substrate, the photolabile protecting group at the C-3' terminus of the first nucleotide is removed via photochemical reaction to form an immobilized nucleotide bearing a C-3' hydroxyl group. Repeated surface activation of the C-3' hydroxyl group via chloro-N,N-diisopropylamine-β-cyanoethoxyphosphine forms the C-3' phosphoramidite on the solid surface and coupling the surface C-3' phosphoramidite with another incoming modified nucleotide having a C-5' hydroxyl group forms an immobilized dinucleotide. Repeated sequences of C-3' photolabile group deprotection, in-situ C-3' surface activation, and phosphoramidite coupling afford the synthesis of oligonucleotides with C-5' attached to the solid substrate. The C-3' terminus of the oligonucleotides remains at the open terminal position. Since the oligonucleotides are attached to the solid surface through C-5' and the C-3' stays at the terminal position, the solid phase supported oligonucleotides are essentially an oligonucleotide on solid support. The solid phase supported primers can then be used with polymerase and DNA templates to form primer extensions.

Using an in-situ deprotecting-activating-coupling synthesis for forming phosphoramidites on the solid phase surface has several advantages. The modified nucleotide monomers in the coupling reactions contain C-5' free hydroxyl groups which are substantially less costly than modified nucleotides having C-5' phosphoramidite groups. The modified nucleotides including a C-5' hydroxyl group can also be re-used since the excess monomers are essentially chemically intact, stable compounds. Unlike the in-situ deprotecting-activating-coupling synthesis, other procedures utilizing modified nucleotides including the phosphoramidite groups require a large excess of the modified nucleotides which decompose after the phosphoramidite containing nucleotides are activated for coupling reactions with tetrazoles. The in-situ deprotecting-activating-coupling synthesis for forming surface bound phosphoramidites is, in general, a quantitative reaction that is usually conducted in methylene chloride with chloro-N,N-diisopropylamine-β-cyanoethoxyphosphine in the presence of a tertiary amine such as diisopropylethyl amine. The phosphoramidite formed on the surface is stable and can be readily used in a subsequent coupling reaction with a modified nucleotide including a C-5' hydroxyl group. The modified nucleotide is dissolved in an organic solvent such as acetonitrile along with catalytic quantities of tetrazole to activate the surface phosphoramidite groups. The excess modified nucleotides including a C-5' hydroxyl group are substantially unaffected by the reaction conditions such that the excess monomeric nucleotide can be recovered and used in subsequent coupling cycles.

Oligonucleotides synthesized via the method of this invention contain nucleotide oligomers in which the C-5' oxygen is covalently attached to the substrate and the C-3' terminus is unobstructed at the opposite end of the chain. In general, the sequence of synthesizing oligonucleotides of this invention is equivalent to natural or biological DNA synthesis, i.e., a C-5' oxygen of a monomeric nucleotide links to the C-3' phosphoramidite activated group. Thus, the immobilized oligonucleotides produced via this invention can be used as a natural primer, for polymerase mediated 3' primer extension reactions with a cDNA template.

As described previously, the method of synthesis of an oligonucleotide in a direction of 5' to 3' also covers a deprotection-activation-coupling oligonucleotide synthesis which consists of a nucleotide or an oligonucleotide having a free terminal C-3' hydroxyl and a terminal C-5' that is blocked by a group, wherein the free terminal C-3' hydroxyl is activated with a phosphorous activating group. The synthesis includes sequentially deprotecting a photolabile protecting group from the C-3' oxygen of a nucleotide at terminus, activating the C-3' oxygen, in situ, with an activating phosphorous group, and coupling another C-3' photolabile protected nucleotides to the activated nucleotide at terminus. The cycles of deprotecting, activating, and coupling are repeated until a desired oligonucleotide is obtained. Typically, the C-3' oxygen is activated with a phosphorous group such as a phosphoramidite, $[(i-Pr)_2N]POCH_2CH_2CN$.

Removal of a photolabile protecting group

The ease of photodeprotection of the photolabile protecting groups at the C-3' position is critical in generating an array of oligonucleotides on the substrate. The deprotection rate depends on the structure of the photo-protecting groups, wavelength and intensity of the incident UV irradiation. Photolysis experiments can be used to screen photo-protecting groups for the desired characterisitics. Table 1 contains results of photolysis experiments for three modified nucleotides, shown below as formulae (5–7) in which the C-3' hydroxyl groups on thymidine are protected separately with 2-nitrovaleryl-oxycarbonyl (NVOC), methyl-6-nitropiperonyloxycarbonyl (MeNPOC) and (R,S)-(1-(3-methoxy-4-benzyloxy-6-nitrophenyl)-ethoxy) carbonyl (MBNPEOC), respectively.

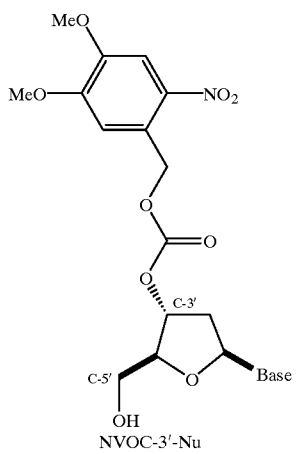

(5)
NVOC-3'-Nu

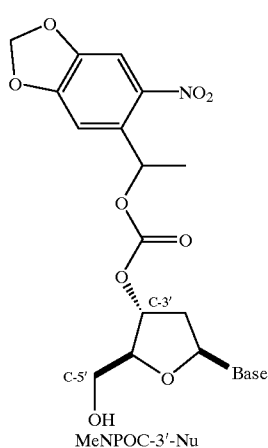

(6)
MeNPOC-3'-Nu

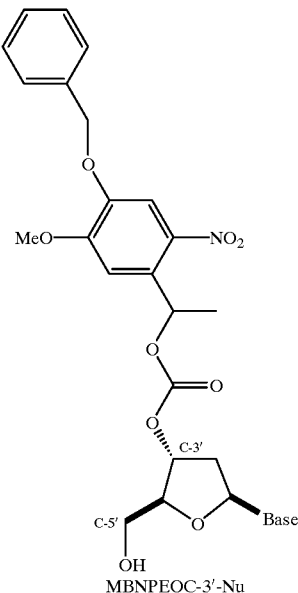

(7)
MBNPEOC-3'-Nu

Comparative photo-deprotection studies include irradiating each compound in dioxane solution at 0.1 mM concentration. The photolysis products are analyzed via reverse phase HPLC using acetonitrile and water buffered at pH 7 as the mobile phase. The UV light source is a 100-watts medium pressure quartz mercury-vapor lamp (Model #7825-30) manufactured by Hanovia. The UV light is filtered to transmit light above the wavelength of 330 nm. The half-life, $T_{1/2}$, is the time in seconds required to deprotect 50% of the photolabile group. As seen in Table 1, the photolabile groups MeNPOC and MBNPEOC have similar deprotection rates.

TABLE 1

Photolysis of 3'-protected Nucleotides

| 3'-Protected Nucleotide | half-life, (s) |
| --- | --- |
| NVOC-3'-Thymidine | 330 |
| eNPOC-3'-Thymidine | 140 |
| MBNPEOC-3'-hymidine | 140 |

Solubility of the C-3' protected compounds in organic solvent such as acetonitrile are also an important factor in making the choice. Compounds such as NVOC-3'-Nucleoside and MeNPOC-3'-Nucleoside are poorly soluble in acetonitrile, whereas MBNPEOC-3'-Nucleoside compounds are readily dissolve in acetonitrile. Due to the high deprotection rate and solubility MBNPEOC relative to NVOC or MeNPOC, MBNPEOC is a desirable photoprotecting group at the C-3' position.

An oligonucleotide array

Additionally, the photolabile protecting groups are attached at the C-3' oxygen of nucleotides so that immobilized oligonucleotides of this invention can be activated by photolithography. In particular, photolithographic techniques can be applied to produce spatially addressable arrays of specific oligonucleotides which, with the C-3' position unobstructed, can be used as arrays of primers to produce primer extensions of cDNA templates. Specifically, semiconductor photolithographic techniques can be used to construct specific oligonucleotide arrays with the C-5' of the first nucleotide attached to the solid phase.

Figure 5:
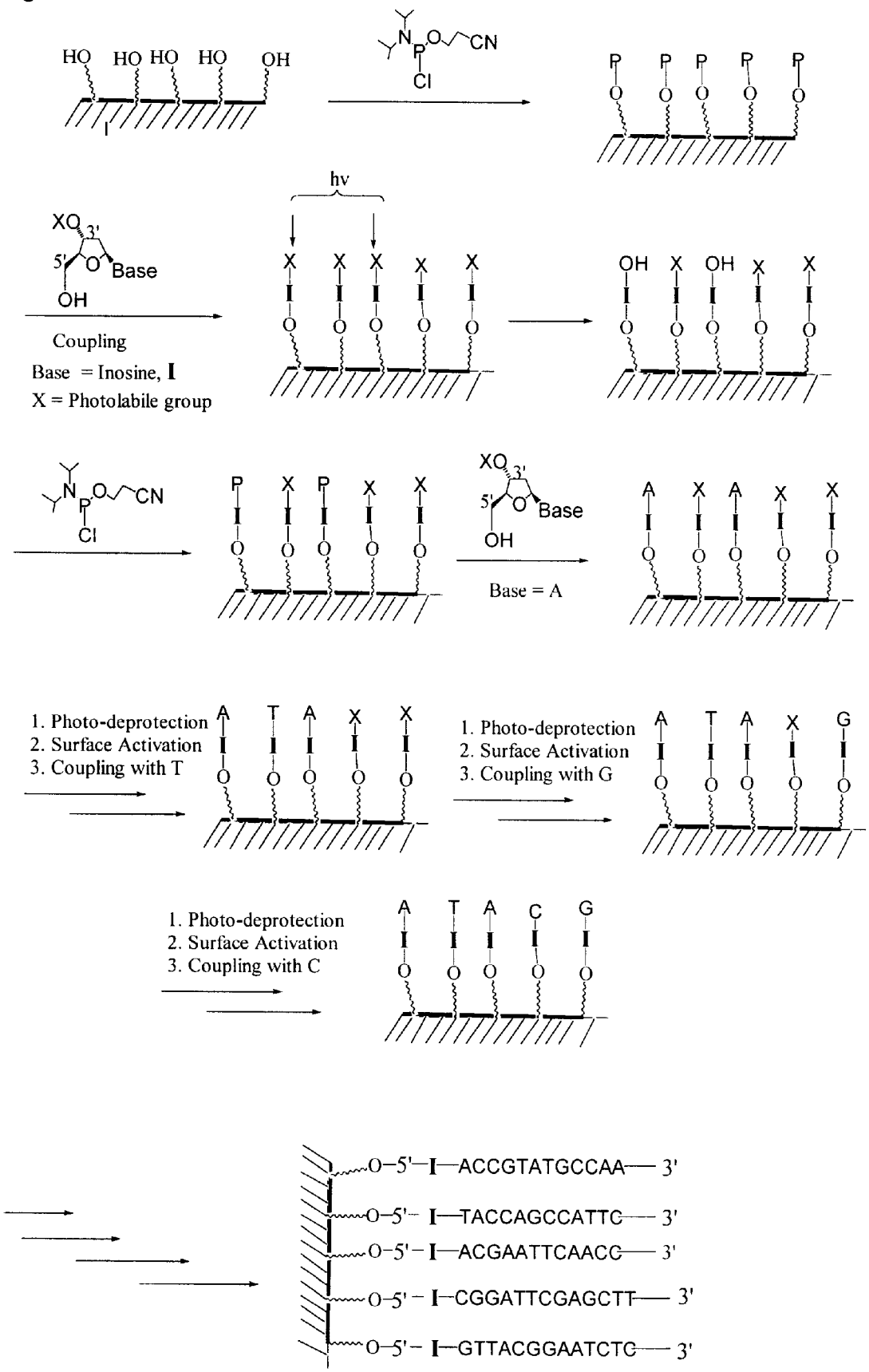
FIG. 5 is a schematic representation of in-situ deprotecting-activating-coupling synthesis of immobilized oligonucleotide arrays using selective photo-irradiation.

Referring to FIG. 5, a spatially selective irradiation technique (e.g., photoligthographic technique) of in situ deprotecting-activating-coupling includes sequential steps of:

(1) deprotecting select regions of a substrate including an array of linking groups, primer nucleotides, oligomers, or a mixture thereof;

(2) activating the C-3' oxygen of the primer nucleotides or the terminal nucleotide of the oligomer in the selected regions, or the terminal oxygen of the linking group in the selected regions with a phosphorous activating group; and (3) coupling specific nucleotides of formula 1, in which P is hydrogen, onto the selectively activated oxygen atoms.

Specifically, a glass substrate bearing polyethylene glycol linker with terminal hydroxyl groups is treated with chloro-N,N-diisopropylamine-β-cyanoethoxyphosphine to form phosphoramidite on the solid surface. Deoxyinosine bearing a C-5' free hydroxyl group and C-3' photolabile group as shown in formula (1), where P is a hydrogen, and is coupled to the solid phase supported phosphoramidite. This coupling reaction results in the attachment of the C-5' of deoxyinosine to the solid surface and the C-3' at the terminal position. A pre-defined portion of the photolabile group at the C-3' position of the deoxyinosine is then removed by pre-defined positional irradiation of UV light to produce a pre-defined portion of free hydroxyl groups at the C-3' position. The use of deoxyinosine as the first base before other nucleotides such as A, T, G, and C usually creates improved stabilization during hybridization of the immobilized oligomer with DNA templates. After the photodeprotection reaction, the freed hydroxyl groups at the C-3' position of the deoxyinosine can be activated with chloro-N,N-diisopropylamine-β-cyanoethoxyphosphine to form C-3' phosphoramidite. Further coupling with another nucleotide containing C-5' free hydroxyl group and C-3' photolabile group forms a dinucleotide on pre-defined positions on the solid support. Repeated selective photodeprotection, surface phosphoramidite formation and coupling with modified nucleotides produces an array of oligonucleotides with C-5' attached to the glass substrate and C-3' at the terminus.

In other embodiments, immobilized nucleotide arrays having C-5' bound to the surface and C-3' at the terminus can be produced by reacting a C-5' activated, C-3' photolabile group protected nucleotide, i.e., a compound of formula 1 in which P is a phosphorous activating group, with a terminal hydroxyl group bound to the surface. For example, after coupling a modified nucleotide to the surface, the C-3' photolabile protecting group can be deprotected via photochemical reaction to form a free hydroxyl group at the C-3' terminus. The hydroxyl group, in turn, can react with a modified nucleotide including a C-5' phosphorous activating group to tether the modified nucleotide to the surface. Repeated selective coupling of modified nucleotides carrying a C-5' phosphorous activating group, such as phosphoramidite, and selective photodeprotection of the C-3' photolabile protecting groups forms immobilized oligonucleotides arrays having C-5' attached to the solid surface and the C-3' at the terminal position.

Selective photo-deprotection can be accomplished by several known methods; photolithography method as disclosed in Science, 251, 767–773, (1991); Proc. Natl. Acad. Sci. USA, 93, 13555–13560, (1996); U.S. Pat. Nos. 5,424,186; 5,510,270; and 5,744,305, and 5,744,101 or using the digital micromirror technique described in "Maskless fabrication of light-directed oligonucleotide microarrays using a digital micromirror array" by Michael Sussman, et. al., Nature Biotechnology, 17, 974–978, (1999). Of course, lithographic techniques also can be used in conjunction with chemical deprotection provided that the chemical conditions for deprotecting the C-3' oxygen do not adversely interact with the lithographic masking materials.

An array having C-5' immobilized oligonucleotides produced via the method of this invention can have a density of at least 10, 50, 100, 200, 500, $10^3$, $10^4$, $10^5$, $10^6$, $10^7$, $10^8$, or $10^9$ addresses per $cm^2$, and/or a density of no more than 10, 50, 100, 200, 500, $10^3$, $10^4$, $10^5$, $10^6$, $10^7$, $10^8$, or $10^9$ addresses/$cm^2$. In a preferred embodiment, the plurality of addresses includes at least 10, 100, 500, 1 000, 5 000, 10 000, or 50 000 addresses. In a preferred embodiment, the plurality of addresses includes less than 9, 99, 499, 999, 4 999, 9 999, or 49 999 addresses. The center to center distance between addresses can be 5 mm, 1 mm, 100 mm, 10 mm, 1 mm, 100 nm, 10 nm, 1 nm or less and/or ranges between. The longest diameter of each address can be 5 mm, 1 mm, 100 mm, 10 mm, 1 mm, 100 nm, 10 nm, 1 nm, 0.1 nm or less, and/or ranges between. In one embodiment, each addresses contains 0 mg, 1 mg, 100 ng, 10 ng, 1 ng, 100 pg, 10 pg, 1 pg, 0.1 pg, or less of the nucleic acid and/or ranges between. In another embodiment, each address contains 100, $10^3$, $10^4$, $10^5$, $10^6$, $10^7$, $10^8$, or $10^9$ or more molecules of the nucleic acid and/or ranges between. Addresses in addition to addresses of the plurality can be disposed on the array.

The oligonucleotide array of this invention can be used to produce gene expression profiles after polymerase mediated primer extension reactions. Immobilized oligomers having designed nucleotide sequences constructed by combining the method of photolithography or other selective light transmission techniques facilitate both gene expression profiling and single nucleotide polymorphism detection. Spatially addressable arrays of a limited number of primers with rationally designed sequences can be constructed by combining the method of photolithography, C-5' immobilized oligonucleotide synthesis, and differential display technology.

Differential display is a valuable tool for elucidating the genes that cause disease. See, for example, U.S. Pat. No. 5,262,311; Liang, P & Pardee, A. B. Science, (1992), 257;967–971; Liang, P & Pardee, A. B. eds. (1997) Methods in Molecular Biology: Differential display Methods and Protocols, Vol 85.). In particular, the mRNA differential display method works by systematic amplification of the 3'-terminal portions of mRNA and resolving those fragments on a DNA sequencing gel using anchored primers designed to bind to the 5' boundary of the poly-A tails for reverse transcription. After PCR amplifying the immobilized nucleotide to include an arbitrary sequence of nucleotides, mRNA populations can be observed by denaturing polyacrylamide electrophoresis. Experimentally, for differential display, an optimal length of arbitrary oligonucleotides added to the immobilized nucleotide primer can be determined under stringent conditions to avoid redundancy of mRNA bands in each cell types (Liang et al., (1994), Nucleic Acid Research, 22, 5763). A rational oligonucleotide design also allows scientists to determine a limited number of arbitrary oligomers containing the optimal length so that most of the mRNA in a mammalian cell is represented (Liang and Pardee, (1994), *Methods in Molecular Genetics*, 5:3).

Despite the fact that numerous novel genes have been identified through the differential display technique, false positives have been frequently encountered by many scientists practicing in the art. The manual steps required to follow the protocols complicate the use of automation. Both intrinsic and extrinsic factors such as quality of reagents and enzymes, type and purity of primers, internal controls chosen, reaction setup and training and experience of a researcher can contribute to potential flaws of false positives (Liang and Pardee, (1994), *Methods in Molecular Genetics*, 5:3).

The oligonucleotide array of this invention along with differential display and DNA chip technology in gene expression monitoring can be used to identify modified genes associated with diseases or screen compounds for drug discovery in a high throughput format.

DNA chip technology in gene expression monitors or accesses genetic information on a large scale by using hybridization of differentially expressed genes on a set of oligonucleotides arrayed in a high density format on substrates. See, for example, Ramsay, G. (1998), *Nature Biotechnology*, 16, 40–44; Bains, W. & Smith, G. C., (1988), *J. Theor. Biol.* 135, 303–307; Drmanac, R. et al., (1989), *Genomics*, 4, 114–128; Shena, M., et al., (1995), *Science*, 270, 467–470. Each oligonucleotide is usually required to have 20 to 28 nucleotide bases in order to maintain a satisfactory specificity. The ability to produce high density microarrays in spatially addressable matrices on a support permits an increase of throughput for large scale hybridization, thus facilitating the identification of genetic information on a single DNA chip. The DNA chip has proven to be a very powerful tool for monitoring gene expression, mapping genomic library clones and resequencing genes to screen for mutations and polymorphisms.

Although the DNA chips permits a genome-wide gene monitoring study, analysis of the hybridization pattern to identify and quantify the cellular abundance of thousands of different RNA molecules is, however, highly convoluted and a sophisticated bio-informatics will be required to elucidate the genetic information. Additionally, the step-wise chemical synthesis of 25-mer oligonucleotides poses a challenge in obtaining a satisfactory overall yield of the desired oligonucleotide. For example, even if the synthesis efficiency of each step is as high as 99%, after 25 steps the overall yields can only reach $0.99^{25}=77.7\%$. Depending on the user requirements, 77.7% overall yields may lead to an unacceptable signal-to-noise ratio for reliable bio-informatic analysis.

An advantage associated with combining the techniques of differential display and spatially addressable oligonucleotide synthesis on solid substrates to study gene expression profiles is the ease of manufacturing capability. Conventional high density microarray DNA chips having oligonucleotides attached to the solid surface through the C-3' terminus, typically, require the oligomers to be longer than 20 bases, preferably between 25 to 28 bases, in order to avoid redundancy (one cDNA is represented in more than one hybridization) and to maintain specificity of hybridization with cDNA from the cell. The number of oligonucleotides required to hybridize most of the genes from a cell is normally in the range of $10^5$ to $10^6$. On the other hand, the optimal length of the oligonucleotides used as primers in this invention would generally require no longer than 14- or 15-mers and only a limited number of primers are needed to cover most of the expressed genes. The technical development of manufacturing DNA chips with a limited number of primers (in the range of 64 to 1000) and shorter oligomers (in the range of 10 to 15 bases long) should be more feasible and the cost of production can also be more reasonable.

The theoretical basis for calculating the limited number of primers was previously reported by Liang & Pardee, 1994, *Methods Molecular Genetics*, 5:3. Therefore, the selected limited number of primers from differential display of a specific cell type will be the same number of oligonucleotides to be synthesized on the support. After primer extension experiments are conducted in the presence of dNTP and cDNA directly on immobilized oligonucleotides or immobilized nucleotide primers, the group of genes that are associated with a particular oligonucleotide will serve as templates for the same oligonucleotide. Therefore, a large percentage of genes will be divided into pools of genes according to the limited number of primers chosen from the study of differential display of expressed genes. For example, if the number of primers required from differential display of expressed genes is 200 and the optimal primer length contains 13 bases, then the solid phase synthesis of the 200 primers with C-5' attached to the solid surface, using the photolithography technique as described in the invention, will produce a matrix of 200 spatially defined C-5' solid surface bound oligonucleotides on solid substrates such as glass slides. After the primer extension reactions using labeled dNTP's, the expressed genes will be grouped into 200 pools according to the primer sequences. With a highly sensitive detection system, a comparison of the signals between the tested and the control samples may indicate changes of the expressed genes within the same primer pools. If the changes are observed, the expressed genes within the pool will be differentially displayed on denatured polyacrylamide gels. The detailed expression profiles will then be used to identify the genes that are modified in the tested samples.

Another useful aspect of the invention is the use of spatially arrayed primers for multiple single nucleotide polymorphism (SNP) analysis. SNPs are the most abundant type of DNA sequence variation in the human genome (Kwok, P -Y., et al., *Genomics*, (1996), 31, 123–126). A SNP is a site on the DNA in which a single base-pair varies from person to person. The mean density of SNPs is approximately one per kb in the human genome. The mutation rate per generation of SNPs is low. SNPs are touted as the genetic markers of choice for the study of complex genetic traits. SNP analysis can be used to create a library revealing disease-associated mutations or a response to medication. This information can be applied to targeting drugs to each unique genetic profile. It is estimated (Risch & Merikangas, (1996), *Science*, 273, 1516–1517) that some 60,000 markers at 50 kb spacing will be needed in an association study with 1,000 individuals (500 patients and 500 controls) and it is likely that a subset of SNPs are functionally important in complex disease traits. SNP libraries will shorten the disease-gene discovery process and initiate an era of personalized medicine.

Since massive numbers of assays need to be performed each day to study samples of a large population, high throughput, efficient, and inexpensive genotyping methods will be necessary. U.S. Pat. No. 5,888,819 describes a method using primer extension reaction to detect SNP with designed terminators of nucleotides. Each of the terminators is capable of specifically terminating the extension in a manner strictly dependent on the identity of the unpaired nucleotide base in the template immediately adjacent to, and downstream of, the C-3' end of the primer. The terminators are also labeled with a detectable marker. U.S. Pat. No. 6,004,744 describes the use of immobilized primers to test SNPs. The primers are oligonucleotides with C-5' terminus biotinylated for binding to the solid surface.

The association study between SNPs and human disease traits or drug responses may be very useful in identifying disease targets to develop diagnostics and drug treatments (pharmacogenomics). It is estimated that more than 300,000 SNPs have been identified. In the human genome, there are thought to be over 200,000 SNPs that lie in genes, and probably 2,000,000 SNPs or more in non-genetic DNA (Collins, F. S. et al., Science, (1997), 278, 1580–1581). To pursue the association study, screening SNPs across different populations can be essential. This would require a massive number of SNP assays considering the number of SNPs and the populations. Highly efficient and inexpensive high throughput SNP assays is urgently needed. The current invention may provide a useful method to conduct multiple SNP screening simultaneously using the spatially arrayed oligonucleotides as described in the invention.

Microarrays are currently being used for gene sequencing studies. The primer arrays described in this invention, however, provide a useful feature that allows on-chip primer extension capability to enhance the accuracy and efficiency of gene expression and sequencing studies.

The invention is further described in the following examples, which do not limit the scope of the invention described in the claims.

EXAMPLE 1

Detecting Surface Activating Groups

Synthesis of primers on glass substrate can be monitored with a fluorescence label such as a cyanine compound (known as Cy3). As shown in formula (8), the cyanine contains two free hydroxyl groups (Cy3-OH).

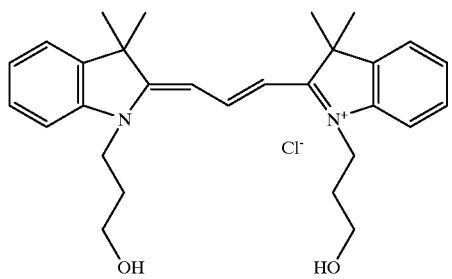

(8)

The free hydroxyl groups can be used to detect the presence of surface bound phosphoramidites. See, for example, FIG. 6. After exposing the subtrate to CY3-OH, the surface was washed with a mixture of methanol/acetone/water (1:1:1) and 0.9 M NaCl, 60 mM NaH2PO4, 6 mM EDTA, pH 7.5, to help distinguish between covalently bound and physically absorbed fluoreacence labels. The relative fluorescence intensity was recorded by scanning the substrate surface with a laser scanner using a Cy3 excitation wavelength at 550 nm. The relative surface fluorescence intensity can also be used to monitor the efficiency of both the photo-deprotection and the coupling of nucleotides.

Referring to FIG. 7, after the polyethylene glycol linker containing glass substrate is activated to give surface bound phosphoramidite groups, the phosphoramidite groups react with Cy3-OH to form a surface fluorescence label as indicated in Row 1. When the surface phosphoramidite is coupled with nucleotides, the surface is covered with photo-protecting groups and no reaction occurs after the surface is exposed to Cy3 -OH. Thus, no surface fluorescence label forms as indicated in Row 2. When the photo-protecting groups of the coupled nucleotides are photochemically removed, the C-3' position forms hydroxyl groups which, in turn, can react with chloro-N,N-diisopropylamine-β-cyanoethoxyphosphine to form surface phosphoramidites. The surface phosphoramidites can be fluorescently labelled as observed again in Row 4.

EXAMPLE 2

Synthesis of (R,S)-1-(3-methoxy-4-benzyloxy-6-nitrophenyl) ethyl chloroformate

Synthesis of 3-hydroxy-4-benzyloxyacetophenone:

15.7 g of 60% NaH were charged to a 1-L4-neck round-bottom flask, washed with 350 mL of hexane, dried under nitrogen gas, and charged with 60 mL of dry DMF. After stirring and cooling under nitrogen in an ice-water bath, 60.0 g of 3-methoxy-4-hydroxy-acetophenone dissolved in 210 mL of dry DMF were added dropwise in about 40 min while the reaction temperature was kept below 15° C. The reaction mixture was stirred at the ice-water temperature for about one hour and 50.1 g of benzyl chloride was added in a slow stream. The cooling bath was removed and the reaction mixture stirred at room temperature over the weekend. After diluting with 650 mL of water, the solids precipitated out were collected, rinsed with 1 liter of water, and dried as much as possible under the water aspirator pressure. 138.33 g of a wet solid were thus obtained. The wet solids were used for the synthesis in the next step without further purification.

Synthesis of 3-hydroxy-4-benzyloxy-6-nitroacetophenone:

69 g of the wet solids from the last step were added in small portions to a stirred mixture of 240 mL 70% nitric acid and 90 mL glacial acetic acid pre-cooled to around 1° C. in an ice-water bath. The addition was completed in about 20 min with temperature kept below 4° C. After stirring at the ice-water temperature for about two hours, the reaction mixture was poured onto 1.2 kg of ice, stirred, and the straw-colored solids collected. The solids were washed with 2 liters of water and dried under the water aspirator pressure as much as possible to give 51.7 g of product, which were used for the synthesis in the next step without further purification.

Synthesis of (R,S)-1-(3-methoxy-4-benzyloxy-6-nitrophenyl)ethanol:

46.5 g of the solid obtained from the last step were dispersed in 405 mL of a 2:1 mixture of methanol and THF, and cooled to about 10–15° C. in an ice-water bath. 7.8 g of sodium borohydride were added over a period of about 20 min. and the reaction temperature was maintained at 10–15° C. After stirring at room temperature for about one hour, the clear solution was cooled in an ice-water bath and 450 mL of 0.5 N HCl and 500 mL of water were added. The yellow solids were collected, dried as much as possible under the water aspirator pressure, and recrystallized from 200 mL of methanol to give 30.5 g of a solid after drying under high vacuum.

$^1$HNMR (CDCl3): δ1.56 (d, 3H), 2.28 (s, 1H), 4.0 (s, 3H), 5.18 (s, 2H), 5.57 (m, 1H), 7.26 (s, 1H), 7.33–7.48 (m, 5H), 7.63 (s, 1H).

Synthesis of (R,S)-1-(3-methoxy-4-benzyloxy-6-nitrophenyl)ethyl chloroformate:

11.1 g of (R,S)-1-(3-methoxy-4-benzyloxy-6-nitrophenyl)ethanol were dissolved in 20 mL of dry THF, after which 60 mL of 20% phosgene in toluene was added. The reaction mixture was stirred at room temperature for about 24 hours, and the excessive phosgene was removed under water aspirator pressure with a caustic trap. After stripping under high vacuum, the brown solids were stirred in about 40 mL of ether, and collected. 7.5 g of an off-white solid were obtained after drying under high vacuum.

$^1$HNMR (CDCl3): δ1.74 (d, 3H), 4.01 (s, 3H), 5.16–5.23 (dd, 2H), 6.58 (quartet, 1H), 7.04 (s, 1H), 7.31-7.48 (m,56H), 7.69 (s, 1H).

EXAMPLE 3

General Procedure for the Synthesis of 3'-O-[(R,S)-(1-(3-methoxy-4-benzyloxy-6-nitrophenyl)ethoxy) carbonyl]-2'-deoxynucleosides Synthesis of 5'-O-TBDMS-3'-O-[(R,S)-(1-(3-methoxy-4-benzyloxy-6-nitrophenyl)-ethoxy)carbonyl]-2'-deoxynucleosides:

1 to 4 equivalents of 60% NaH were charged to a dry reactor, washed with hexane, dried under the nitrogen atmosphere, and then covered with enough dry solvents such as THF or N-methyl-pyrrolidinone (NMP). The NaH in the dry solvent was stirred and cooled in an ice-water bath under the nitrogen atmosphere, and added dropwise about 0.8 to 1.2 equivalents of the 5'-O-TBDMS-2'-deoxynucleoside dissolved in a dry solvent in about 10 to 30 min. After stirring at the ice-water temperature or at the ambient temperature for about 0.5 to 3 hr, about 0.8 to 1.2 equivalents of (R,S)-1-(3-methoxy-4-benzyloxy-6-nitrophenyl)ethyl chloroformate dissolved in a dry solvent was added in about 5 to 30 min. The reaction mixture was stirred at the ice-water bath temperature for about 10 min to about 18 hr, and then acidified with acid and worked up in water and an appropriate organic solvent such as methylene chloride or ethyl acetate. The organic layer was separated and stripped to give a light yellow solid which may be purified by eluting through a column packed with silica gel as needed.

Synthesis of 3'-O-[(R,S)-(1-(3-methoxy-4-benzyloxy-6-nitrophenyl)-ethoxy) carbonyl]-2'-deoxynucleosides:

The 5'-O-TBDMS-3'-O-((R,S)-1-(3-methoxy-4-benzyloxy-6-nitrophenyl)-ethoxy)-carbonyl-2'-deoxynucleosides prepared above was dissolved in THF, cooled in an ice-water bath, and added about 1.5 to 5 equivalents of 1 M tetrabutylammonium fluoride solution in THF. After stirring at the ice-water temperature or at the ambient temperature for about 10 to 120 min., the reaction mixture was diluted with water to precipitate out either a yellow solid or an oily material. The solids were collected, washed with some water, and dried under high vacuum to give the desired product. The oily material may be dissolved in an organic solvent, washed with some water and/or brine, dried with a drying agent, and stripped and dried under high vacuum to give a yellow solid of the desired product.

EXAMPLE 4

Synthesis of 5'-O-TBDMS-3'-O-[(R,S)-(1-(3-methoxy-4-benzyloxy-6-nitrophenyl)-ethoxy) carbonyl]-N$^6$-benzoyl-2'-deoxyadenosine 195 mg (4.9 mmol) of 60% NaH was charged to a 20 mL dry reactor, washed with 10 mL of dry hexane, dried under the nitrogen atmosphere, and covered with 2 mL of dry THF (distilled from NaH). The NaH in THF was stirred and cooled in an ice-water bath. 2 g (4.3 mmol) 5'-O-TBDMS-N$^6$-benzoyl-2'-deoxyadenosine dissolved in 5 mL of dry THF were added dropwise in about 12 min. After stirring at the ice-water temperature for about 52 min., 1.7 g (4.8 mmol) of (R,S)-1-(3-methoxy-4-benzyloxy-6-nitrophenyl) ethyl chloroformate dissolved in about 4 mL of dry THF were added in about 18 min. The reaction mixture was stirred at the ice-water temperature for about 75 min., quenched with 3 drops of acetic acid, and stripped to give a solid residue. The residue was purified by eluting through a silica gel column. A total of 1.06 g of the desired product was obtained. Synthesis of 3'-O-[(R,S)-(1-(3-methoxy-4-benzyloxy-6-nitrophenyl)-ethoxy) carbonyl]-N$^6$-benzoyl-2'-deoxyadenosine:

0.94 g (1.2 mmol) of 5'-O-TBDMS-3'-O-((R,S)-1-(3-methoxy-4-benzyloxy-6-nitrophenyl)-ethoxy)carbonyl-N$^6$-benzoyl-2'-deoxyadenosine was dissolved in 7 mL of THF, cooled in an ice-water bath and added 2.4 mL of 1 M tetrabutylammonium fluoride in THF. After stirring at the ice-water temperature for about 1.5 hr, the reaction mixture was quenched with 30 mL of water, stripped of THF, and extracted 3 times with 10 mL of methylene chloride. The combined methylene chloride layers were washed 3 times with 1:1 brine—water, dried over with anhydrous MgSO$_4$, filtered, and removed most of the solvent by stripping. The oily residue was diluted with hexane to give a straw-colored solid. The solids were collected, washed with some hexane, and dried under high vacuum to give 0.66 g solids of the desired product.

$^1$HNMR (CDCl3): δ1.71 (d, 3H), 2.5 (m, 1H), 3.2 (m, 1H), 3.86 (quartet, 1H), 3.95 (quartet, 1H), 4.0 (s, 3H), 4.26 (s, 1/2H), 4.35 (s, 1/2H), 5.20 (s, 2H), 5.45 (m, 1H), 5.84 (t, 1H), 6.35 (m, 1H), 6.44 (quartet, 1 H), 7.08 (s, 1H), 7.3–7.7 (m, 9H), 8.02 (d, 2H), 8.07 (d, 1H), 8.78 (s, 1H), 9.02 (s, 1H).

EXAMPLE 5

Synthesis of 5'-O-TBDMS-3'-O-[(R,S)-(1-(3-methoxy-4-benzyloxy-6-nitrophenyl)-ethoxy) carbonyl]-N$^4$-benzoyl-2'-deoxycytidine 200 mg (5.0 mmol) of 60% NaH was charged to a 20 mL dry reactor, washed with 10 mL of hexane, dried under nitrogen atmosphere, and covered with 2 mL of dry THF (distilled from NaH). The NaH in THF was stirred and cooled in an ice-water bath. 2 g of (4.5 mmol) 5'-O-TBDMS-N$^4$-benzoyl-2'-deoxycytidine dissolved in 5 mL of dry THF were added dropwise in about 18 min. After stirring at the ice-water temperature for about 60 min., 1.74 g (5.0 mmol) of (R,S)-1-(3-methoxy-4-benzyloxy-6-nitrophenyl)-ethyl chloroformate dissolved in about 4 mL of dry THF were added in about 24 min. The reaction mixture was stirred at the ice-water temperature for about 60 min., quenched with 2 drops of acetic acid, and stripped to give a solid residue. The residue was dissolved in 15 mL of ethyl acetate, washed 3 times with 6 mL of 1:1 brine—water, dried over anhydrous MgSO$_4$, filtered, and stripped to give 3.2 g of a yellow solid. The yellow solid was purified by eluting through a silica gel column with 2:1 hexane—ethyl acetate and 1:2 hexane—ethyl acetate. A total of 1.75 g of the desired product was obtained.

EXAMPLE 6

Synthesis of 3'-O-[(R,S)-(1-(3-methoxy-4-benzyloxy-6-nitrophenyl)ethoxy)-carbonyl]-N$^4$-benzoyl-2'-deoxycytidine 1.64 g (2.1 mmol) 5'-O-TBDMS-3'-O-[(R,S)-(1-(3-methoxy-4-benzyloxy-6-nitrophenyl)-ethoxy)carbonyl]-N$^4$- benzoyl-2'-deoxycytidine was dissolved in 8 mL of THF, and cooled in an ice-water bath. 4.5 mL of 1 M tetrabutylammonium fluoride in THF was added to the cooled solution. After stirring at the ice-water temperature for about 2 hr the reaction mixture was quenched with 200 mL of water to give a light yellow-colored solid. The solids were collected, rinsed with an additional 50 mL of water, dried under high vacuum, and dissolved in methylene chloride to remove the insoluble solid. After stripping off the solvent, about 0.45 g of the desired product was obtained.

$^1$HNMR (CDCl3): δ1.67 (d, 3H), 2.40 (m, 1H), 2.70 (m, 1H), 2.85 (s, 1H), 3.80–4.0 (m, 2H), 4.02 (s, 3H), 4.29 (s, 1H), 5.18 (s, 2H), 5.26 (m, 1H), 6.28 (m, 1H), 6.40 (quartet, 1H), 7.07 (s, 1H), 7.30–7.64 (m, 10 H), 7.66 (s, 1H), 7.87 (d, 2H), 8.24 (d, 1H), 8,74 (s, 1H).

EXAMPLE 7

Synthesis of 3'-O-[(R,S)-(1-(3-methoxy-4-benzyloxy-6-nitrophenyl)ethoxy)-carbonyl]-N$^2$-isobutyryl-2'-deoxyguanosine 20 mg (0.5 mmol) of 60% NaH was charged to a 6 mL dry reactor and covered with 0.2 mL of dry NMP (distilled from CaH$_2$). The NaH in NMP was stirred and cooled in an ice-water bath. 100 mg (0.22 mmol) 5'-O-TBDMS-N$^2$-isobutyryl-2'-deoxyguanosine dissolved in 0.6 mL of dry NMP were added dropwise in about 3 min. After stirring at room for 25 min., a very thick paste was formed. 1.5 mL more of dry NMP were added, and the reaction mixture was stirred at room temperature for another 2 hr. and then cooled in an ice-water bath. 80 mg (0.23 mmol) of (R,S)-1-(3-methoxy-4-benzyloxy-6-nitrophenyl)-ethyl chloroformate dissolved in about 0.3 mL of dry THF were added in about 11 min. After storing in the refrigerator overnight, the reaction mixture was acidified with acetic acid, and poured into 15 mL of water to yield a solid. The solids were collected, dissolved in methylene chloride, dried over anhydrous MgSO$_4$, filtered, and stripped of the solvent to produce 124 mg of a yellow solid. 76 mg of the yellow solid was dissolved in 1 mL of THF, cooled in an ice-water bath and added 220 μL of 1 M tetrabutylammonium fluoride in THF. After stirring at the ice-water temperature for about 35 min., the reaction mixture was quenched with water, stripped and purified by column. 10 mg of the desired product was obtained after eluting with 2:1 ethyl acetate—hexane and 40:1 ethyl acetate—methanol.

$^1$HNMR (CDCl3): δ1.25 (d, 6H), 1.70 (d, 3H), 2.45 (m, 1H), 2.66 (m, 1H), 2.98 (m, 1H), 3.76–3.98 (m, 2H), 4.0 (s, 3H), 4.17 (s, 1/2H), 4.26 (s, 1/2H), 5.06 (m, 1H), 5.18 (s, 2H), 5.35 (m, 1H), 6.10 (m, 1H), 6.42 (m, 1H), 7.07 (s, 1H), 7.30–7.48 (m, 5H), 7.65 (s, 1/2H), 7.66 (s, 1/2H), 8.73 (s, 1H), 12.15 (s, 1H),

EXAMPLE 8

Synthesis of 3'-O-[(R,S)-(1-(3-methoxy-4-benzyloxy-6-nitrophenyl)ethoxy)-carbonyl]-thymidine 500 mg of 60% NaH was charged to a 50 mL reactor, washed with 10 mL of hexane, and covered with 5 mL of dry THF. The NaH in THF was stirred and cooled in an ice-water bath under the nitrogen atmosphere. 2.0 g of 5'-O-TBDMS-thymidine dissolved in 10 ml of dry THF was added dropwise to the cooled, stirred solution. After the dropwise addition was complete, the reaction mixture was stirred at room temperature for about 30 min. and then cooled in an ice-water bath. 1.86 g of (R,S)-1-(3-methoxy-4-benzyloxy-6-nitrophenyl)-ethyl chloroformate dissolved in 20 ml of dry THF was added. The reaction mixture was stirred at room temperature for about 1 hr, after which 3 mL of acetic acid and 120 mL of ethyl acetate were added. After washing 3 times with 30 mL of water, the ethyl acetate solution was dried over anhydrous MgSO$_4$, filtered, and stripped to give an oily residue. The oily residue was purified by a silica gel column to give 2.23 g of 5'-O-TBDMS-3'-O-(R,S)-(1-(3-methoxy-4-benzyloxy-6-nitrophenyl)-ethoxy)carbonyl-thymidine. 2.23 g of 5'-O-TBDMS-3'-O-(R,S)-(1-(3-methoxy-4-benzyloxy-6-nitrophenyl)-ethoxy)carbonyl-thymidine were dissolved in 30 mL of THF along with 6.7 mL of 1M tetrabutylammonium fluoride in THF. After stirring at room temperature for about 1 hr, the reaction mixture was diluted with 120 mL of ethyl acetate, washed 2 times with 30 mL of water, dried over anhydrous MgSO$_4$, and stripped to give an oily residue. The addition of hexane to the oily residue induced the precipitation of a light yellow solid, which was collected to give 1.15 g of the desired product after drying under high vacuum.

$^1$H-NMR (CDCl$_3$): δ1.68 (d, 3H) 1.92 (s, 3H), 2.4 (m, 2H), 3.80–3.95 (m, 2H), 4.0 (s, 3H), 4.02–4.60 (m, 1H), 5.15–5.30 (m, 3H), 6.25 (m, 1H), 6.4 (m, 1H), 7.063 (s, 1H), 7.3–7.5 (m, 6H), 7.66 (d, 1H), 8.26 (s, 1H).

Synthesis of 3'-O-[(1-(3,4-dimethoxy-6-nitrophenyl) ethoxy)-carbonyl]-thymidine:

A procedure similar to those described in Example 8 was used to prepare the above compound. The structure was characterized below with NMR.

$^1$H-NMR (DMSO-d$_6$): δ1.76 (s, 3H), 2.30 (m, 1H), 3.61 (m, 1H), 3.85 (s, 3H), 3.90 (s, 3H), 4.1 (m, 2H), 5.2 (m, 2H), 5.50 (s, 2H), 6.2 (m, 1H), 7.2 (s, 1H), 7.70 (s, 1H), 7.71 (s, 1H), 11.3 9 (s, 1H).

EXAMPLE 9

Synthesis of 3'-O-[(R,S)-(1-(3-methoxy-4-benzyloxy-6-nitrophenyl)ethoxy)-carbonyl]-2'-deoxynucleoside-5'-O-(2-cyanoethyl N,N-diiospropylphosphoramidite)

Synthesis of 3'-O-[(R,S)-(1-(3-methoxy-4-benzyloxy-6-nitrophenyl)-ethoxy) carbonyl]-N$^6$-benzoyl-2'-deoxyadenosine-5'-O-(2-cyanoethyl N,N-diiospropylphosphoramidite):

20 mg (0.029 mmol) of 3'-O-[(R,S)-(1-(3-methoxy-4-benzyloxy-6-nitrophenyl)-ethoxy)carbonyl]-N$^6$-benzoyl-2'-deoxyadenosine was charged to a 6 mL reaction vial, along with 0.5 mL of dry methylene chloride, 10 μL (0.057 mmol) of diisopropylethylamine, and 7 μL (0.031 mmol) of 2-cyanoethyl N,N-diisopropylchlorophophoramidite. The reaction mixture was stirred at room temperature for about 45 min, then diluted with 1 mL of methylene chloride and washed with 1 mL of 1:1 brine—water. After drying and filtering, the methylene chloride solution was stripped and dried under high vacuum to give 21 mg solids of the desired product.

$^1$H-NMR (CDCl$_3$): δ1.67 (m, 12H), 1.70 (d, 3H), 2.65–2.90 (m, 2H), 3.58 (m, 2H), 3.7–4.0 (m, 6H), 4.03 (s, 3H), 4.30 & 4.41 (2s, 1H), 5.20 (s, 2H), 5.37 (m, 1H), 6.45 (m, 1H), 6.65 (m, 1H), 7.10 (s, 1H), 7.30–7.70 (m, 9H), 8.05 (d, 2H), 8.48 (d, 1H), 8.81 (s, 1H), 9.04 (s, 1H).

Synthesis of 3'-O-[(1-(3,4-dimethoxy-6-nitrophenyl) ethoxy)-carbonyl]-thymidine:

A procedure similar to those described in Example 9 was used to prepare the above compound. The structure was characterized below with NMR.

$^1$H-NMR (DMSO-d$_6$): δ1.76 (s, 3H), 2.30 (m, 1 H), 3.61 (m, 1H), 3.85 (s, 3H), 3.90 (s, 3H), 4.1 (m, 2H), 5.2 (m, 2H), 5.50 (s, 2H), 6.2 (m, 1H), 7.2 (s, 1H), 7.70 (s, 1H), 7.71 (s, 1H), 11.3 9 (s, 1H).

EXAMPLE 10

Synthesis of 5'-O-TBDMS-3'-O-[(R,S)-(1-(3,4-(methylenedioxy-6-nitrophenyl)-ethoxy)carbonyl]-thymidine 49 mg (1.2 mmol) of 60% NaH was charged to a 6 mL dry reactor, washed with 4 mL of dry hexane, dried under the nitrogen atmosphere, and covered with 0.3 mL of dry THF (distilled from NaH). The NaH in THF was stirred and cooled in an ice-water bath. 200 mg (0.56 mmol) of 5'-O-TBDMS-thymidine dissolved in 0.5 mL of dry THF was added dropwise in about 7 min. After stirring at the ice-water temperature for about 3 hr., 160 mg (0.58 mmol) of (R,S)-1-(3,4-(methylenedioxy)-6-nitrophenyl)ethyl chloroformate dissolved in about 0.6 mL of dry THF were added in about 4 min. The reaction mixture was stirred at the ice-water temperature for about 2.5 hr. and room temperature for about 2 hr., quenched with 4 drops of acetic acid, diluted with 2 ml of water and stripped off THF. Extraction with 4 mL of methylene chloride, followed by drying over anhydrous MgSO$_4$, filtration and stripping, gave 265 mg of a yellow solid. The yellow solid was purified by column to give 183 mg of the desired solid.

Synthesis of 3'-O-[(R,S)-(1-(3,4-(methylenedioxy)-6-nitrophenyl)ethoxy)carbonyl]-thymidine:

50 mg (0.084 mmol) of 5'-O-TBDMS-3'-O-[(R,S)-(1-(3,4-(methylenedioxy)-6-nitrophenyl)ethoxy)carbonyl]-thymidine was dissolved in 1 mL of dry THF, stirred in an ice-water bath, and added 168 μL of 1 M tetrabutylammonium fluoride in THF. After stirring at the ice-water temperature for about 3 hr., the reaction mixture was diluted with 3 mL of water, stripped off THF, and extracted with 6 mL of methylene chloride. The methylene chloride layer was dried over anhydrous MgSO$_4$, filtered, and stripped to give 36 mg of a yellow solid of the desired product.

$^1$H-NMR (CDCl$_3$): 1.66 (d, 3H), 1.90 (s, 3H), 2.43 (m, 2H), 3.74 (t, 1H), 3.91 (m, 2H), 4.08 & 4.16 (2s, 1H), 5.22 (s, 1H), 6.27 (s, 2H), 6.22 (m, 1H), 6.28 (m, 1H), 7.06 (s, 1H), 7.49 (s, 2H), 8.90 (s, 1H).

EXAMPLE 11

Preparation of Solid Substrate Supported Phosphoramidite on the Terminal Position of Linker Molecules Glass microscopic slides were cleaned with acetone, methanol, and water before being treated with 6 N HCl overnight. The treated glass slides were washed thoroughly with di-ionized water and methanol. The glass slides were dried at 100° C. for 2 hours. In a moisture-free chamber a solution prepared from 40% of dimethyldichlorosilane, SiMe$_2$Cl$_2$ in pyridine was used to react with the pre-treated glass slides for two hours. After the silane treatment, the glass slides were rinsed with methylene chloride and immediately immersed into a solution prepared from 42 ml of PEG 400 (polyethylene glycol, average molecular weight of 400) and 2 ml DBU (1,8-Diazabicyclo[5,4,0]undec-7ene) and agitated on a shaker overnight. To quantify the surface coating, the resulting pegylated glass slides were treated with a solution prepared from 2 grams of para-dimethoxytritylchloride in 50 ml of pyridine. The dmt (dimethoxytrityl) coated glass slides were washed thoroughly with acetone, methylene chloride, and methanol. The dmt can be cleaved from the glass surface by treating the glass slides with 2% dichloroacetic acid in methylene chloride. The cleaved dmt solution was analyzed with UV-Visible spectrophotometry at 530 nm. The pegylated glass slides were treated in a solution prepared from 0.5 ml of chloro-N,N-diisopropylamine-β-cyanoethoxyphosphine, 1.5 ml of DIPEA and 3 ml of methylene chloride for 5 minutes. Phosphoramidite was formed in-situ at the terminal position of the linker molecule. The density of the surface phosphoramidite can be quantified with fluorescence label, Cy3-OH (3). The fluorescent labeling solution was prepared from dissolving 50 mg of Cy3-OH and 8 mg of tetrazole in dried acetonitrile.

EXAMPLE 12

Figure 6:
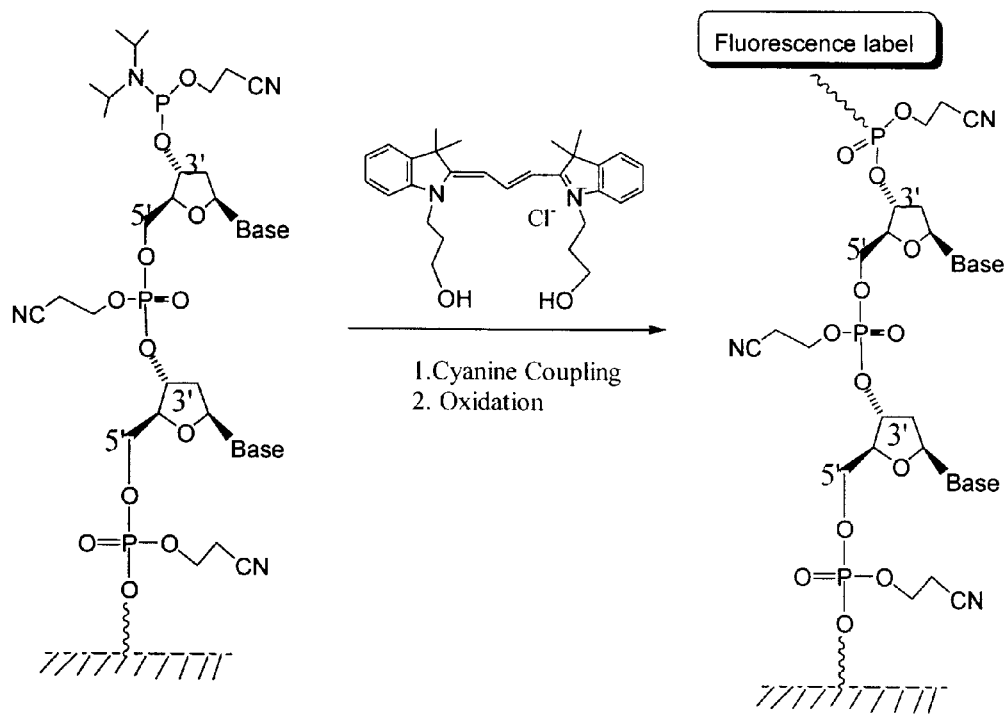
FIG. 6 depicts a fluorescein-labeled immobilized nucleotide.

Coupling of Substrate Supported Phosphoramidite with Monomeric Nucleotide Containing C-5' Hydroxyl, C-3' Photoprotecting Group Glass slides covalently coated with phosphoramidite prepared from the previous example were immersed in a solution containing 50 mg of monomeric nucleotides synthesized in Example 2, 8 mg of tetrazole and 1 ml of P$_2$O$_5$ dried acetonitrile for 2 minutes. The nucleotide/tetrazole solution was removed and collected for future use. The glass slides were washed with acetonitrile, methylene chloride and methanol. Oxidation was accomplished with an iodine solution prepared from 50 mM of iodine in a THF/Pyridine/Water 93:5:2 ratio. The C-3' photo-protecting group was removed using UV irradiation in dioxane at wavelength above 330 nm for 5 minutes. The glass slides were treated again with a solution prepared from 0.5 ml of chloro-N,N-diisopropylamine-β-cyanoethoxyphosphine, 1.5 ml of DIPEA and 3 ml of methylene chloride for 5 minutes. The surface phosphoramidite was analyzed after coupling with Cy3 -OH using the same solution prepared in Example 6. The C-3' phosphoramidite on the solid substrate was used to couple with the C-5' hydroxyl group of the next monomeric nucleotide. The repetitive sequence of "photo-deprotection, surface phosphoramidite activation and nucleotide coupling" produced solid phase supported primer as shown in FIG. 6.

All the chemical reagents used in the Examples were obtained from commercial sources (Aldrich Chemical Co., Milwaukee, Wis. and Sigma Chemical Co., Milwaukee, Wis.). The intermediates and the products were identified by mass spectrometry and $^1$H-NMR. Analysis of fluorescence labels were performed using a laser scanner, ScanArray, manufactured by GSI Lumonics.

A number of embodiments of the invention have been described. Nevertheless, it will be understood that various modifications may be made without departing from the spirit and scope of the invention. For example, the synthesis of producing immobilized oligonucleotides C-5' bound to a solid substrate and C-3' at the terminus position can also be applied to produce oligonucleotides having C-3' bound to the solid support and C-5' at the terminus position such as by synthesizing monomeric nucleotides including a C-3' hydroxyl group and C-5' photo-protecting group. Other aspects, advantages, and modifications are within the scope of the claims.

What is claimed is:

1. A method of producing an immobilized oligonucleotide on a substrate comprising:

covalently attaching a first nucleotide or an oligonucleotide via a C-5' oxygen of the nucleotide to a hydroxyl group that is activated with a phosphorous activating group and immobilized on the substrate.

2. The method of claim 1, wherein the first nucleotide has the formula

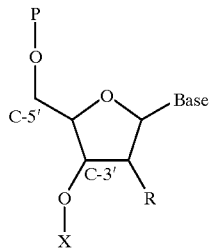

wherein X is selected from the group consisting of a photolabile protecting group and a chemically labile protecting group; R is selected from the group consisting of hydrogen, hydroxyl, and modified hydroxyl; P is hydrogen and Base is selected from the group consisting of a pyrimidine and a purine.

3. The method of claim 2 further including removing the photolabile protecting group or the chemically labile protecting group from the C-3' oxygen of the first nucleotide to form a hydroxyl group.

4. The method of claim 3 further including activating the C-3' hydroxyl group of the first nucleotide with a phosphorous activating group.

5. The method of claim 4 further including covalently attaching a second nucleotide monomer or oligonucleotide via a C-5' oxygen of a nucleotide to the first nucleotide.

6. The method of claim 5, wherein the phosphorous activating group is N,N-diisopropylamine-β-cyanoethoxphosphine.

7. The method of claim 2, wherein the base is selected from the group consisting of adenyl, guanyl, cytidyl, thymidyl, inosyl, and uridyl.

8. The method of claim 7, wherein the base is inosyl.

9. The method of claim 2, wherein X is a photolabile protecting group selected from the group consisting of 2-nitrovaleryl-oxycarbonyl (NVOC), methyl-6- nitropiperonyloxycarbonyl (MeNPOC) and (R,S)-(1-(3-methoxy-4-benzyloxy-6-nitrophenyl)- ethoxy) carbonyl (MBNPEOC).

10. The method of claim 9, wherein X is (R,S)-(1-(3-methoxy-4- benzyloxy-6-nitrophenyl)-ethoxy) carbonyl (MBNPEOC).

11. The method of claim 2, wherein the first nucleotide has the formula

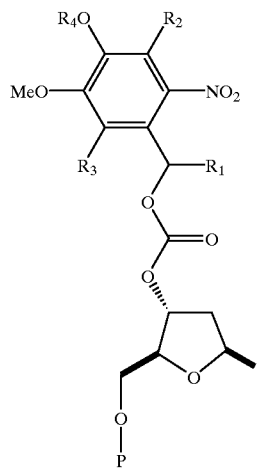

wherein $R_1$, $R_2$, $R_3$ each independently is selected from the group consisting of hydrogen, C1–C10 alkyl, C2–C10 alkenyl, aryl, benzyl, and C1–C10 alkoxyl; $R_4$ is selected from the group consisting of C1–C10 alkyl, C2–C10 alkenyl, aryl, and benzyl; and P is hydrogen.

12. The method of claim 1, wherein the activated hydroxyl group is attached to the terminal end of a linking group immobilized on a substrate.

13. The method of claim 12, wherein the linking group has the formula $(OCH_2CH_2)n$—O— and n has value between about 3 and about 30.

14. The method of claim 1, wherein the substrate is selected from the group consisting of glass, surface-modified glass, particles, and shaped gel.

15. The method of claim 1, wherein the phosphorous activating group is chloro-N,N-diisopropylamine-b-cyanoethoxyphosphine or bis-N,N-diisopropylamine-b-cyanoethoxyphosphine.

16. A method of synthesizing an oligonucleotide on a substrate, comprising:

(a) contacting a modified nucleotide via a C-5' oxygen to an activated immobilized hydroxyl group to produce a covalently attached nucleotide, wherein the modified nucleotide includes a C-3' photolabile protecting group and a C-5' hydroxyl group, and wherein the activated immobilized hydroxyl group is activated with a phosphorous activating group;

(b) irradiating the covalently attached nucleotide to remove the C-3' photolabile protecting group and form a C-3' hydroxyl group;

(c) contacting the C-3' hydroxyl group of the covalently attached nucleotide with a phosphorous activating group to produce an activated immobilized hydroxyl group at the C-3' position of the covalently attached nucleotide; and (d) repeating steps (a) to (c).-

17. The method of claim 16, wherein the modified nucleotides have the formula

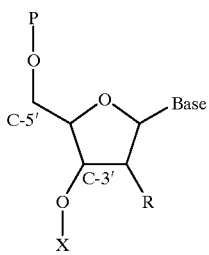

wherein X is a photolabile protecting group; R is selected from the group consisting of hydrogen, hydroxyl, and modified hydroxyl; P is hydrogen; and Base is selected from the group consisting of a pyrimidine, and a purine.

18. The method of claim 16, wherein the phosphorous activating group is chloro-N,N-diisopropylamine-β-cyanoethoxyphosphine or bis-N,N-diisopropylamine-β-cyanoethoxyphosphine.

19. The method of claim 16, wherein the surface hydroxyl group is the terminus of a linking group having the formula (OCH$_2$CH$_2$)n—O—H and n has value between about 3 and about 30.

20. The method of claim 16, wherein the base is selected from the group consisting of adenyl, guanyl, cytidyl, thymidyl, inosyl, and uridyl.

21. The method of claim 16, wherein the photolabile protecting group is selected from the group consisting of 2-nitrovaleryl-oxycarbonyl (NVOC), methyl-6- nitropiperonyloxycarbonyl (MeNPOC) and (R,S)-(1-(3-methoxy-4-benzyloxy-6-nitrophenyl)- ethoxy) carbonyl (MBNPEOC).

22. The method of claim 21, wherein the photolabile protecting group is (R,S)-(1-(3-methoxy-4-benzyloxy-6-nitrophenyl)-ethoxy) carbonyl (MBNPEOC).

23. The method of claim 16, wherein the modified nucleotide has the formula

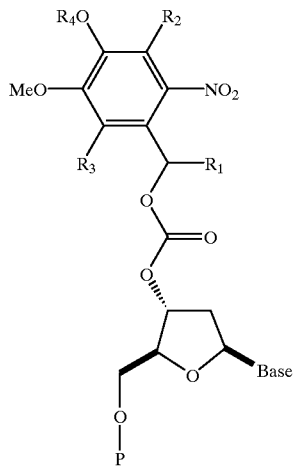

wherein R$_1$, R$_2$, R$_3$ each independently is selected from the group consisting of hydrogen, C1–C10 alkyl, C2–C10 alkenyl, aryl, benzyl, and C1–C10 alkoxy; R$_4$ is selected from the group consisting of C1–C10 alkyl, C2–C10 alkenyl, aryl, and benzyl; and P is hydrogen.

24. A method of claim 16 further including contacting the synthesized oligonucleotide with a polymerase, wherein the polymerase is selected from a group consisting of DNA polymerases and RNA polymerases.

25. A method of claim 16, wherein the substrate is selected from the group consisting of glass, surface-modified glass, particles, and shaped gel.

26. A method of synthesizing an oligonucleotide, comprising:

(a) providing a nucleotide or an oligonucleotide having a free terminal C-3' hydroxyl and a terminal C-5' that is blocked by a group, wherein the free terminal C-3' hydroxyl is activated with a phosphorous activating group;

(b) covalently coupling a modified nucleotide via a C-5' oxygen to the activated hydroxyl group, wherein the modified nucleotide includes a C-3' photolabile protected group and a C-5' hydroxyl group;

(c) irradiating the covalently attached nucleotide to remove the C-3' photolabile protecting group and form a C-3' hydroxyl group;

(d) contacting the C-3' hydroxyl group of the covalently attached nucleotide with a phosphorous activating group to produce an activated hydroxyl group at the C-3' position;

(e) covalently coupling a modified nucleotide via a C-5' oxygen to the activated hydroxyl group of a previously covalently attached nucleotide; and (f) repeating steps (c) to (e).

27. The method of claim 26, wherein the modified nucleotide has the formula

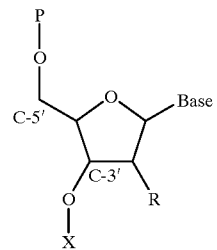

wherein X is a photolabile protecting group; R is selected from the group consisting of hydrogen, hydroxyl, and modified hydroxyl; P is hydrogen; and Base is selected from the group consisting of a pyrimidine and a purine.

28. The method of claim 27, wherein the base is selected from the group consisting of adenyl, guanyl, cytidyl, thymidyl, inosyl, and uridyl.

29. The method of claim 27, wherein the photolabile protecting group is selected from the group consisting of 2-nitrovaleryl-oxycarbonyl (NVOC), methyl-6- nitropiperonyloxycarbonyl (MeNPOC) and (R,S)-(1-(3methoxy-4-benzyloxy-6-nitrophenyl)- ethoxy) carbonyl (MBNPEOC).

30. The method of claim 27, wherein the photolabile protecting group is (R,S)-(1-(3-methoxy-4-benzyloxy-6-nitrophenyl)-ethoxy) carbonyl (MBNPEOC).

31. The method of claim 26, wherein modified nucleotides have the formula

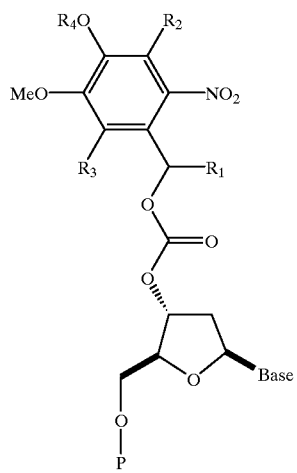

wherein $R_1$, $R_2$, $R_3$ each independently is selected from the group conisisting of hydrogen, C1–C10 alkyl, C2–C10 alkenyl, aryl, benzyl, and C1–C10 alkoxy; $R_4$ is selected from the group consisting of C1–C10 alkyl, C2–C10 alkenyl, aryl, and benyl; and P is hydrogen.

32. A method comprising:
providing a linker group attached to a planar substrate, the linker group comprising a terminal hydroxyl;
activating the terminal hydroxyl with a phosphorous activating group; and
covalently attaching a first nucleotide or an oligonucleotide via a C-5' oxygen of the nucleotide to the terminal hydroxyl.

33. The method of claim 32, in which the activating step is conducted in a solution including methylene chloride.

34. The method of claim 33, in which the activating step is conducted in a solution including a tertiary amine.

35. The method of claim 34 in which the tertiary amine is diisopropylethyl amine.

36. The method of claim 32 in which the phosphorous activating group is -N,N-diisopropylamine-β-cyanoethoxyphosphine.

37. The method of claim 32 in which the first nucleotide or the oligonucleotide is dissolved in an organic solvent.

38. The method of claim 37 in which the organic solvent is acetonitrile.

39. The method of claim 37 in which the organic solvent comprises catalytic quantities of tetrazole.

* * * * *